US009226858B2

(12) United States Patent
Hamilton et al.

(10) Patent No.: US 9,226,858 B2
(45) Date of Patent: Jan. 5, 2016

(54) APPARATUS AND METHOD FOR MAKING A LAYERED ELASTIC SUBSTRATE

(71) Applicant: The Procter & Gamble Company, Cincinnati, OH (US)

(72) Inventors: Raymond Scott Hamilton, Lebanon, OH (US); Mark Mason Hargett, Liberty Township, OH (US); Tina Brown, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 197 days.

(21) Appl. No.: 13/929,878

(22) Filed: Jun. 28, 2013

(65) Prior Publication Data

US 2014/0000794 A1 Jan. 2, 2014

Related U.S. Application Data

(60) Provisional application No. 61/665,945, filed on Jun. 29, 2012.

(51) Int. Cl.
*A61F 13/49* (2006.01)
*A61F 13/15* (2006.01)

(52) U.S. Cl.
CPC ..... *A61F 13/15699* (2013.01); *A61F 13/15593* (2013.01); *A61F 13/49011* (2013.01);
(Continued)

(58) Field of Classification Search
CPC ............ B65H 2801/57; B32B 2555/02; Y10T 156/1011; Y10T 156/1015; Y10T 156/1051; Y10T 156/1052; A61F 13/49011; A61F 13/49012; A61F 13/4902; A61F 13/49022; A61F 13/49023; A61F 13/49025; A61F 13/15325; A61F 13/15601

USPC ................................. 156/164, 229, 494–496
See application file for complete search history.

(56) References Cited

U.S. PATENT DOCUMENTS 3,848,594 A 11/1974 Buell
3,860,003 A 1/1975 Buell
(Continued)

FOREIGN PATENT DOCUMENTS

EP 0 565 606 B1 3/1995
WO WO 95/16746 6/1995
(Continued)

OTHER PUBLICATIONS

PCT/US2013/048390 International Search Report dated Aug. 26, 2013, 12 pages.
(Continued)

*Primary Examiner* — Carson Gross
(74) *Attorney, Agent, or Firm* — Sarah M. DeCristofaro; Abbey A. Lopes

(57) ABSTRACT

A first elastic material is advanced in a machine direction in a stretched state to a first metering device at a speed, V1. A second elastic material is advanced in the machine direction in a stretched state to a second metering device at a speed, V2. First and second substrate layers are advanced in a machine direction to a third metering at a speed, V3, along with the first and second elastic materials. The first and second elastic materials are bonded to the first and second substrate layers at the third metering device to form a layered elastic substrate. The layered elastic substrate is advanced to a fourth metering device at a speed, V4. V1 is less than V2, V3 is greater than V1 and V2, V4 is less than V3, and V4 is greater than V1 and V2.

20 Claims, 18 Drawing Sheets

(52) U.S. Cl.
CPC . *A61F13/49012* (2013.01); *A61F 2013/49028* (2013.01); *B32B 2555/02* (2013.01); *B65H 2801/57* (2013.01); *Y10T 156/1011* (2015.01); *Y10T 156/1015* (2015.01); *Y10T 156/1052* (2015.01)

(56) References Cited

U.S. PATENT DOCUMENTS

| | | | |
|---|---|---|---|
| 3,911,173 A | 10/1975 | Sprague, Jr. | |
| 3,929,135 A | 12/1975 | Thompson | |
| 4,324,246 A | 4/1982 | Mullane et al. | |
| 4,342,314 A | 8/1982 | Radel et al. | |
| 4,381,781 A | 5/1983 | Sciaraffa et al. | |
| 4,463,045 A | 7/1984 | Ahr et al. | |
| 4,573,986 A | 3/1986 | Minetola et al. | |
| 4,609,518 A | 9/1986 | Curro et al. | |
| 4,610,678 A | 9/1986 | Weisman et al. | |
| 4,629,643 A | 12/1986 | Curro et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,785,996 A | 11/1988 | Ziecker et al. | |
| 4,795,454 A | 1/1989 | Dragoo | |
| 4,808,178 A | 2/1989 | Aziz et al. | |
| 4,834,735 A | 5/1989 | Alemany et al. | |
| 4,842,666 A | 6/1989 | Werenicz | |
| 4,846,815 A | 7/1989 | Scripps | |
| 4,857,067 A | 8/1989 | Wood et al. | |
| 4,888,231 A | 12/1989 | Angstadt | |
| 4,894,060 A | 1/1990 | Nestegard | |
| 4,909,803 A | 3/1990 | Aziz et al. | |
| 4,925,520 A * | 5/1990 | Beaudoin et al. | 156/494 |
| 4,946,527 A | 8/1990 | Battrell | |
| 4,963,140 A | 10/1990 | Robertson et al. | |
| 4,988,344 A | 1/1991 | Reising et al. | |
| 4,988,345 A | 1/1991 | Reising | |
| 5,006,394 A | 4/1991 | Baird | |
| 5,137,537 A | 8/1992 | Herron et al. | |
| 5,147,345 A | 9/1992 | Young et al. | |
| 5,151,092 A | 9/1992 | Buell et al. | |
| 5,221,274 A | 6/1993 | Buell et al. | |
| 5,260,345 A | 11/1993 | Desmarais et al. | |
| 5,342,338 A | 8/1994 | Roe | |
| 5,387,207 A | 2/1995 | Dyer et al. | |
| 5,518,801 A | 5/1996 | Chappell et al. | |
| 5,562,646 A | 10/1996 | Goldman et al. | |
| 5,571,096 A | 11/1996 | Dobrin et al. | |
| 5,580,411 A | 12/1996 | Nease et al. | |
| 5,595,567 A | 1/1997 | King et al. | |
| 5,624,427 A | 4/1997 | Bergman et al. | |
| 5,650,222 A | 7/1997 | Desmarais et al. | |
| 5,669,894 A | 9/1997 | Goldman et al. | |
| 5,674,216 A | 10/1997 | Buell et al. | |
| 5,691,035 A | 11/1997 | Chappell et al. | |
| 5,693,165 A | 12/1997 | Schmitz | |
| 5,723,087 A | 3/1998 | Chappell et al. | |
| 5,735,840 A | 4/1998 | Kline et al. | |
| 5,745,922 A | 5/1998 | Rajala et al. | |
| 5,865,823 A | 2/1999 | Curro | |
| 5,916,663 A | 6/1999 | Chappell et al. | |
| 5,928,212 A | 7/1999 | Kline et al. | |
| 5,941,864 A | 8/1999 | Roe | |
| 6,004,306 A | 12/1999 | Roe et al. | |
| 6,010,491 A | 1/2000 | Roe et al. | |
| 6,027,483 A | 2/2000 | Chappell et al. | |
| 6,251,097 B1 | 6/2001 | Kline et al. | |
| 6,414,215 B1 | 7/2002 | Roe | |
| 6,432,098 B1 | 8/2002 | Kline et al. | |
| 6,441,266 B1 | 8/2002 | Dyer et al. | |
| 6,554,815 B1 * | 4/2003 | Umebayashi | 604/385.27 |
| 6,573,423 B1 | 6/2003 | Herrlein et al. | |
| 6,596,108 B2 | 7/2003 | McCabe | |
| 6,677,258 B2 | 1/2004 | Carroll et al. | |
| 7,569,039 B2 | 8/2009 | Matsuda et al. | |
| 8,377,249 B2 | 2/2013 | Gill | |
| 2001/0025683 A1 * | 10/2001 | Burriss et al. | 156/163 |
| 2002/0009940 A1 * | 1/2002 | May et al. | 442/328 |
| 2005/0013975 A1 * | 1/2005 | Brock et al. | 428/198 |
| 2005/0107764 A1 | 5/2005 | Matsuda et al. | |
| 2005/0215963 A1 | 9/2005 | Roe et al. | |
| 2005/0215964 A1 | 9/2005 | Roe et al. | |
| 2005/0215972 A1 | 9/2005 | Roe et al. | |
| 2005/0215973 A1 | 9/2005 | Roe et al. | |
| 2006/0083893 A1 * | 4/2006 | Ashraf | 428/131 |
| 2006/0189956 A1 | 8/2006 | Catalan | |
| 2007/0078427 A1 | 4/2007 | Raycheck et al. | |
| 2007/0093769 A1 | 4/2007 | Kline et al. | |
| 2007/0142798 A1 | 6/2007 | Goodlander et al. | |
| 2007/0142806 A1 | 6/2007 | Roe et al. | |
| 2007/0219521 A1 | 9/2007 | Hird et al. | |
| 2007/0287348 A1 | 12/2007 | Autran et al. | |
| 2007/0287982 A1 | 12/2007 | Lodge et al. | |
| 2007/0287983 A1 | 12/2007 | Lodge et al. | |
| 2008/0132865 A1 | 6/2008 | Li et al. | |
| 2009/0099542 A1 | 4/2009 | Thomas et al. | |
| 2009/0294044 A1 | 12/2009 | Gill | |
| 2010/0252603 A1 | 10/2010 | Gill | |
| 2011/0094669 A1 | 4/2011 | Oetjen | |
| 2011/0139657 A1 | 6/2011 | Hird et al. | |
| 2011/0139658 A1 | 6/2011 | Hird et al. | |
| 2011/0139659 A1 | 6/2011 | Hird et al. | |
| 2011/0139662 A1 | 6/2011 | Hird et al. | |
| 2011/0152812 A1 | 6/2011 | Hird et al. | |
| 2012/0061015 A1 | 3/2012 | LaVon et al. | |
| 2012/0061016 A1 | 3/2012 | LaVon et al. | |
| 2012/0273129 A1 | 11/2012 | Handziak | |
| 2012/0330263 A1 | 12/2012 | Lawson et al. | |

FOREIGN PATENT DOCUMENTS

| | | |
|---|---|---|
| WO | WO 96/24319 A1 | 8/1996 |
| WO | WO 00/02727 A1 | 1/2000 |
| WO | WO 2006/015141 | 2/2006 |
| WO | WO 2007/070138 A1 | 6/2007 |
| WO | WO 2009/146307 A1 | 12/2009 |
| WO | WO 2010/050867 A1 | 5/2010 |
| WO | WO 2010/151195 A1 | 12/2010 |
| WO | WO 2012/177400 A1 | 12/2012 |

OTHER PUBLICATIONS

U.S. Appl. No. 13/929,854, filed Jun. 28, 2013, Mark Mason Hargett.
U.S. Appl. No. 13/929,869, filed Jun. 28, 2013, Raymond Scott Hamilton.

* cited by examiner

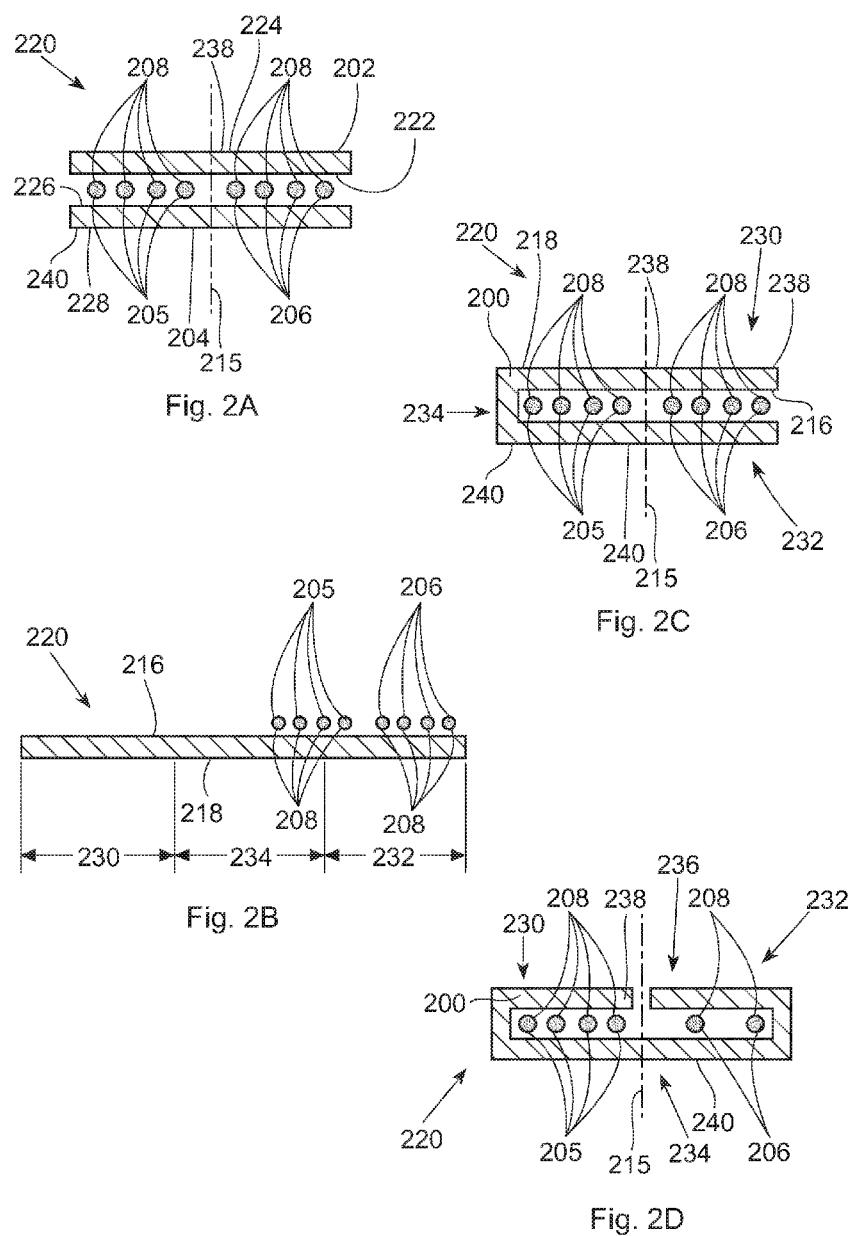

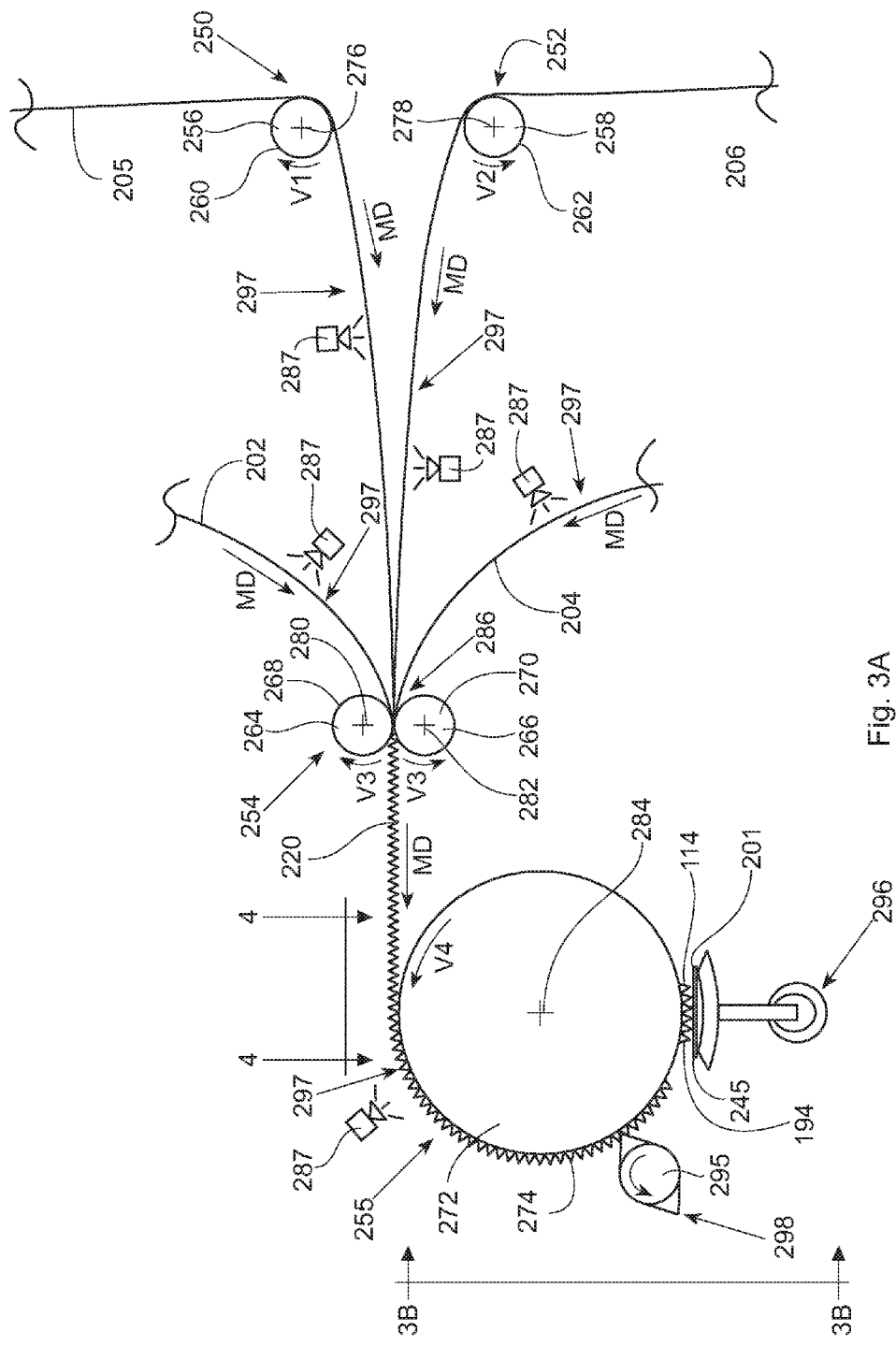

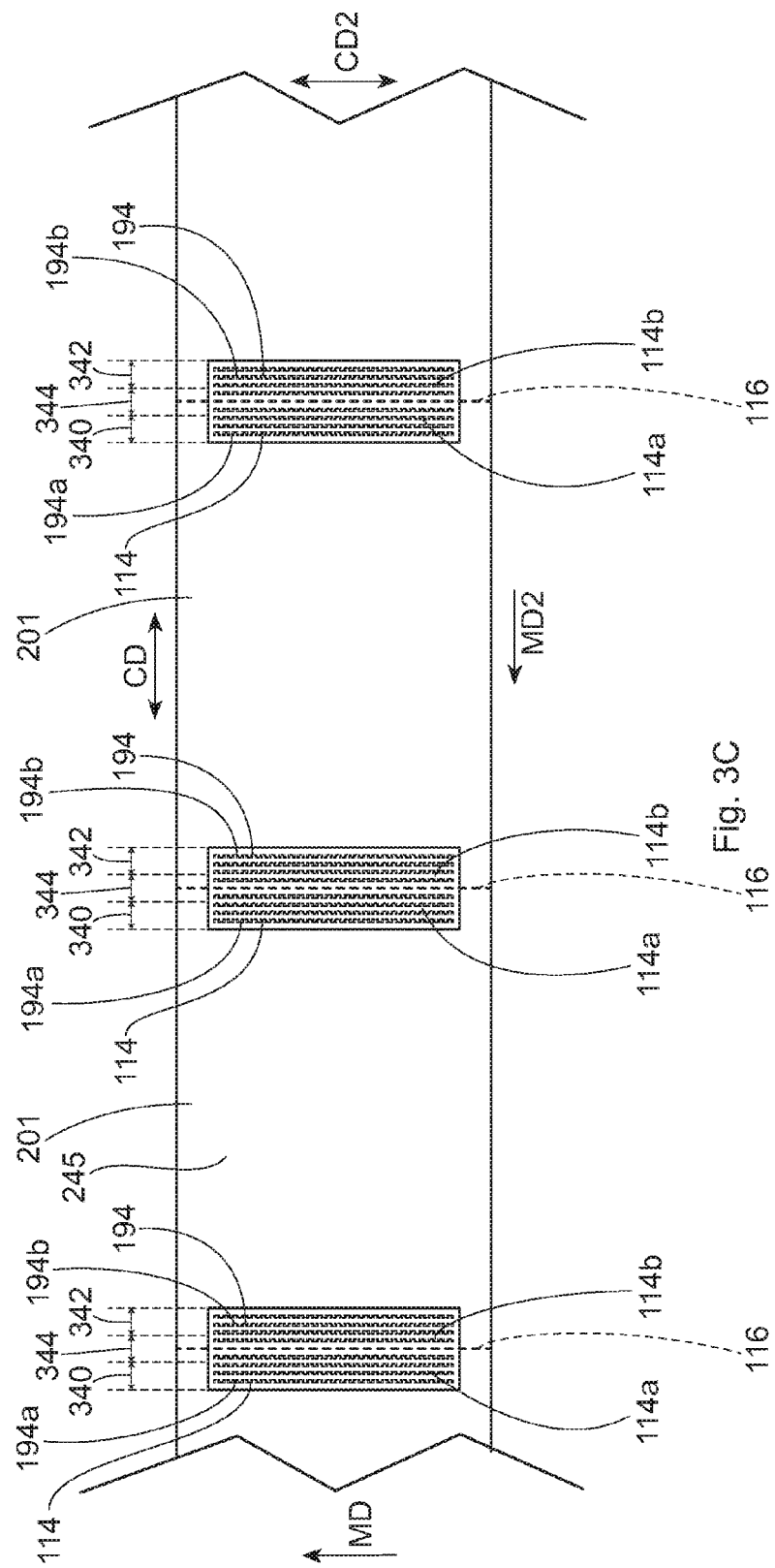

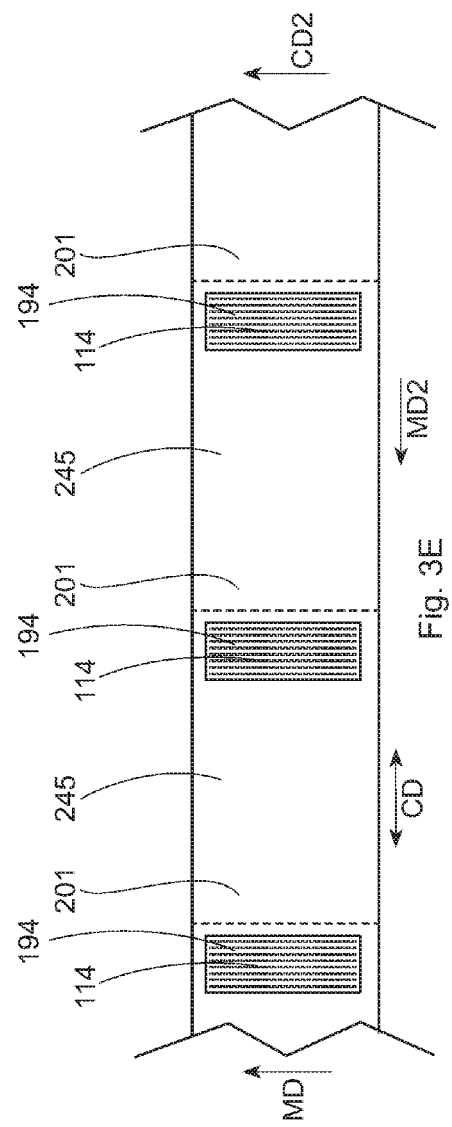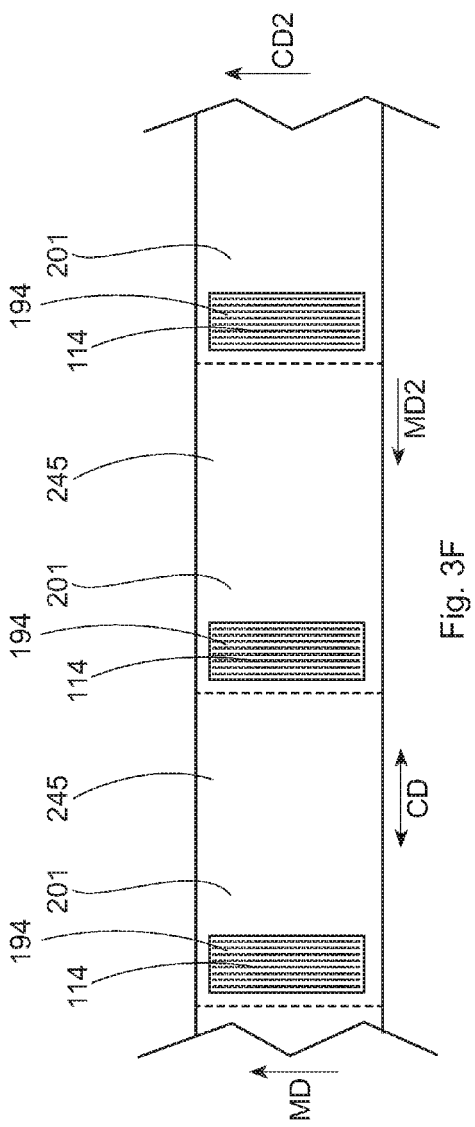

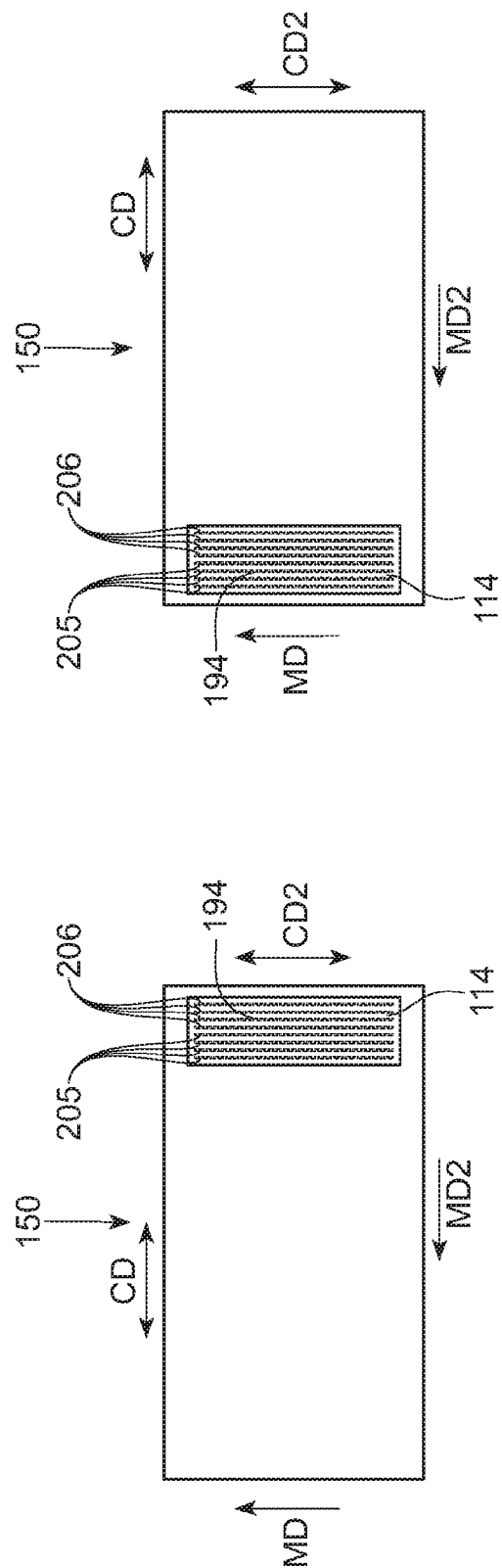

APPARATUS AND METHOD FOR MAKING A LAYERED ELASTIC SUBSTRATE

FIELD OF THE INVENTION

The present disclosure relates to methods for manufacturing absorbent articles, and more particularly, to an apparatus and method for making discrete lengths of layered elastic substrate that may be used as components of absorbent articles.

BACKGROUND OF THE INVENTION

Along an assembly line, various types of articles, such as, diapers and other absorbent articles, may be assembled by adding components to and/or otherwise modifying an advancing, continuous web of material. In some processes, advancing webs of material are combined with other advancing webs of material. In other processes, individual components created from advancing webs of material are combined with advancing webs of material, which in turn, are then combined with other advancing webs of material. In some cases, individual components created from advancing webs are combined with other individual components created from other advancing webs. Webs of material and component parts used to manufacture diapers may include: backsheets, topsheets, leg cuffs, waistbands, absorbent core components, front and/or back ears, fastening components, and various types of elastic webs and components such as leg elastics, barrier leg cuff elastics, stretch side panels, and waist elastics. Once the desired component parts are assembled, the advancing webs and component parts are subjected to a final knife cut to separate the webs into discrete diapers or other absorbent articles.

In some instances, contraction around the waist of a wearer may improve the actual and/or perceived fit of the absorbent article. In some processes, waistbands are bonded to absorbent articles to improve the perceived fit of the absorbent article. Some absorbent articles may have a waistband in a front waist region and a waistband in a back waist region. The waistbands may include an elastic material bonded to one or more layers of nonwoven substrate. In some processes, the elastic material for the front and back waistbands may be stretched to the same elongation. As a result, the front and back waistbands may have the same contraction.

In some instances, it may be desirable to provide a back waistband having more contraction than the front waistband in order to improve the actual and/or perceived fit of the absorbent article on the wearer. However, forming and attaching multiple waistbands having different amounts of contraction may add cost and complexity to the assembly process. Therefore, it would be beneficial to provide a method and apparatus for making a single layered elastic substrate that may be cut into two waistbands having different amounts of contraction.

SUMMARY OF THE INVENTION

In some aspects, the present disclosure relates to a method for making a layered elastic substrate. The method may comprise the steps of: advancing a first elastic material in a machine direction to a first metering device at a speed, $V1$, wherein the first elastic material is in a stretched state; advancing a second elastic material in the machine direction to a second metering device at a speed, $V2$, wherein the second elastic material is in a stretched state; advancing a first substrate layer in the machine direction, the first substrate layer having a first surface and an opposing second surface; advancing a second substrate layer in the machine direction, the second substrate layer having a first surface and an opposing second surface; advancing the first elastic material, the second elastic material, the first substrate layer and the second substrate layer to a third metering device at a speed, $V3$; bonding the first and second elastic materials in the stretched states to the first surface of the first substrate layer and the first surface of the second substrate layer at the third metering device to form a layered elastic substrate; and advancing the layered elastic substrate through a fourth metering device at a speed, $V4$, wherein $V1$ is less than $V2$, wherein $V3$ is greater than $V1$ and $V2$, wherein $V4$ is less than $V3$, and wherein $V4$ is greater than $V1$ and $V2$.

In some aspects, the method may comprise the steps of: advancing a first elastic material in a machine direction to a first metering device at a speed, $V1$, wherein the first elastic material is in a stretched state; advancing a second elastic material in the machine direction to a second metering device at a speed, $V2$, wherein the second elastic material is in a stretched state; advancing a continuous substrate in the machine direction, the substrate having a first surface and an opposing second surface, the substrate defining a first edge region and a second edge region separated by a inner region along a cross direction; folding the substrate to position the first surface of the first edge region into a facing relationship with the first surface of the inner region; folding the substrate to position the first surface of the second edge region into a facing relationship with the first surface of the inner region; advancing the first elastic material, the second elastic material, the first substrate layer and the second substrate layer to a third metering device at a speed, $V3$; bonding the first and second elastic materials in the stretched states to the first surface of the first substrate layer and the first surface of the second substrate layer at the third metering device to form a layered elastic substrate; and advancing the layered elastic substrate through a fourth metering device at a speed, $V4$, wherein $V1$ is less than $V2$, wherein $V3$ is greater than $V1$ and $V2$, wherein $V4$ is less than $V3$, and wherein $V4$ is greater than $V1$ and $V2$.

BRIEF DESCRIPTION OF THE DRAWINGS

FIG. 2A is a schematic, sectional view of a continuous length of layered elastic substrate having elastic strands.

FIG. 2B is a schematic, sectional view of a continuous length of layered elastic substrate having elastic strands.

FIG. 2C is a schematic, sectional view of a continuous length of layered elastic substrate having elastic strands.

FIG. 2D is a schematic, sectional view of a continuous length of layered elastic substrate having elastic strands.

FIG. 3A is a schematic, side elevation view of a converting apparatus for making a layered elastic substrates in the form of discrete waistbands for absorbent articles.

FIG. 3C is a schematic, plan view of a continuous length of absorbent articles having discrete elastic waistbands taken along line 3C-3C of FIG. 3B.

FIG. 3E is a schematic, plan view of a continuous length of absorbent articles having discrete elastic waistbands.

FIG. 3F is a schematic, plan view of a continuous length of absorbent articles having discrete elastic waistbands.

FIG. 3G is a schematic, plan view of a discrete absorbent article having one discrete elastic waistband.

FIG. 3H is a schematic, plan view of a discrete absorbent article having one discrete elastic waistband.

DETAILED DESCRIPTION OF THE INVENTION

Figure 1:
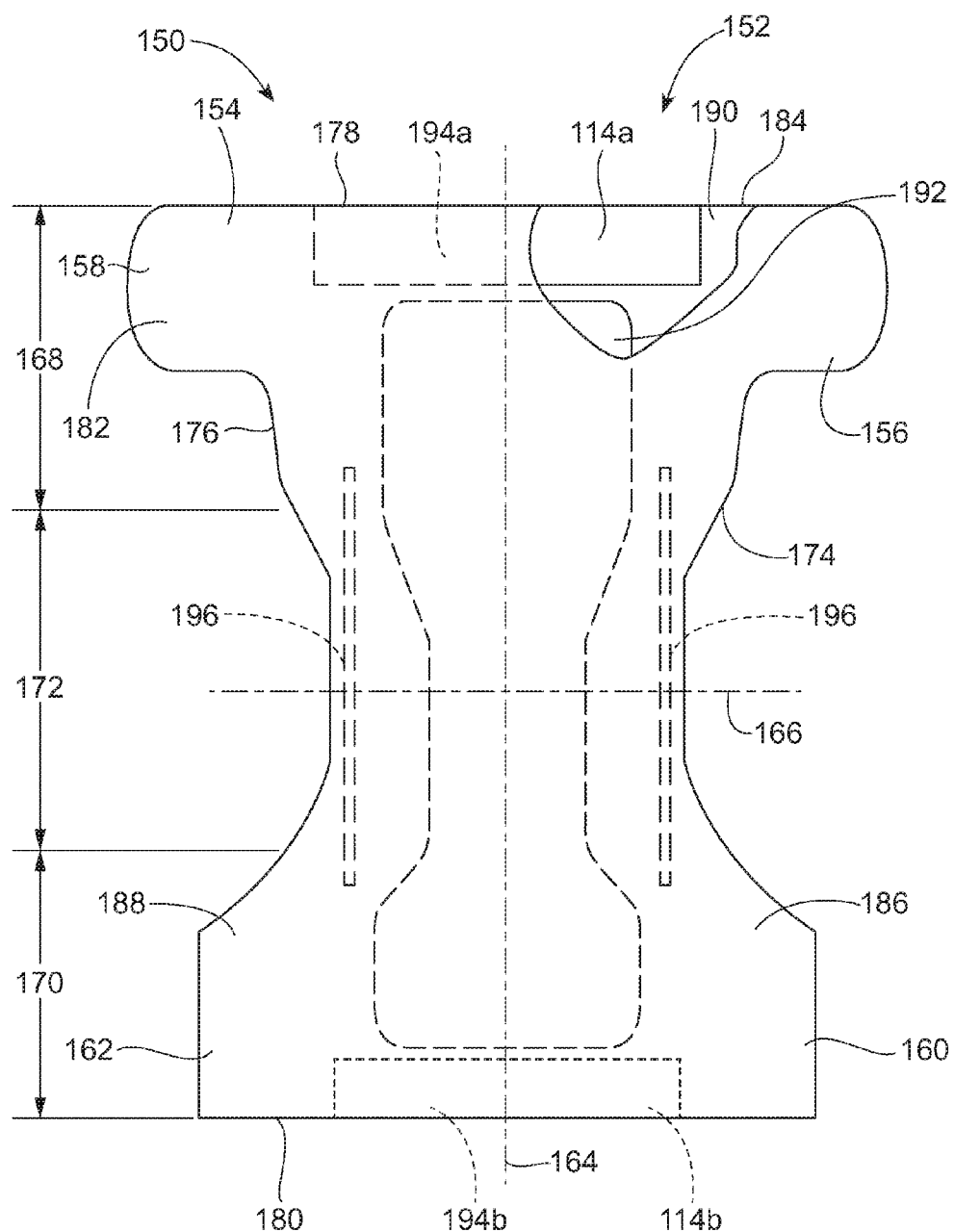
FIG. 1 is a partially cut-away, plan view of a disposable absorbent article having discrete elastic waistbands.

This application claims the benefit of U.S. Provisional Application Ser. No. 61/665,945, filed Jun. 29, 2012, which is hereby incorporated by reference in its entirety.

The following definitions may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Substrate" is used herein to describe a material which is primarily two-dimensional (i.e. in an XY plane) and whose thickness (in a Z direction) is relatively small (i.e. 1/10 or less) in comparison to the material's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers bonded together. As such, a web is a substrate. A substrate may be elastic, inelastic, or extensible.

"Nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

"Machine direction" (MD) is used herein to refer to the direction of material flow through a process. In addition, relative placement and movement of material can be described as flowing in the machine direction through a process from upstream in the process to downstream in the process.

"Cross direction" (CD) is used herein to refer to a direction that is not parallel with, and usually perpendicular to, the machine direction.

"Radial" means a direction running from an axis of rotation of a drum toward an outer circumferential surface of the drum.

"Vacuum pressure" refers to a pressure applied to a discrete length of layered elastic substrate from radially inward from an outer circumferential surface of a drum. Vacuum pressure is a pressure below atmospheric air pressure.

"Elastic," "elastomer" or "elastomeric" refers to a material that upon application of a force to the material's relaxed, initial length can stretch or elongate to an elongated length more than 10% greater than the material's initial length and will substantially recover back to about the material's initial length upon release of the applied force. The term "inelastic" refers herein to any material that does not fall within the definition of "elastic."

"Stretchable" refers to materials that are capable of extending in at least one direction to a certain degree without undue rupture.

"Consolidation" and "consolidated" refers to a material undergoing a reduction in elongation from a first stretched length to a second stretched length that is less than the first stretched length and greater than zero.

"Relaxed state" defines a length of material when not stretched by an applied force.

"Stretched state" defines a length of material that is undergoing an increase in elongation as a result of an applied force.

In the context of the present description, an elongation of 0% refers to a material in relaxed state having a relaxed length of L, and elongation of 150% represents 2.5× the relaxed length, L, of the material. For example, an elastic strand having a relaxed length of 100 millimeters would have a length of 250 millimeters at 150% elongation. And an elastic strand having a relaxed length of 100 millimeters would have a length of 180 millimeters at 80% elongation.

"Contraction" refers to an amount of force per unit length that is required to return an elastic material, or a layered elastic substrate comprising an elastic material, to a fully stretched state.

"Film" refers to a sheet-like material wherein the length and width of the material far exceed the thickness of the material. Typically, films have a thickness of about 0.5 mm or less.

"Extendibility" and "extensible" mean that the width or length of a component in a relaxed state can be extended or increased.

The present disclosure relates to methods for assembling absorbent articles, and more particularly, to methods for making a layered elastic substrate that may be used as elastic waistbands for absorbent articles. A method for making a layered elastic substrate may include advancing a first elastic material in a machine direction to a first metering device at a speed, V1. The first elastic may advance in a stretched state. The method may include advancing a second elastic material in the machine direction to a second metering device at a speed, V2. The second elastic material may advance in a stretched state. The second speed, V2, may be greater than the speed, V1. The method may include advancing first and second substrate layers in a machine direction, the first and second substrate layers having a first surface and an opposing second surface. The first elastic material, the second elastic material, and the first and second substrate layers may advance to a third metering device at a speed, V3. The first elastic material may be stretched to a first elongation between the first and third metering device. The second elastic material may be stretched to a second elongation between the second and third metering devices. The first elongation may be greater than the second elongation. The first and second elastic may be bonded in the stretched state to the first surface of the first substrate layer and the first surface of the second substrate layer at the third metering device to form a layered elastic substrate. The layered elastic substrate may advance to a fourth metering device at a speed, V4. The speed, V3, may be greater than the speeds, V1 and V2. The speed, V4, may be greater than the speeds, V1 and V2, and the speed, V4, may be less than the speed, V3.

The first elastic material of the layered elastic substrate may be consolidated from the first elongation to a second elongation between the third and fourth metering devices. The second elastic material of the layered elastic substrate may be consolidated from the second elongation to a fourth elongation between the third and fourth metering devices. It is to be appreciated that the third elongation may be greater than the fourth elongation. Gathers form in the layered elastic substrate as a result of joining the stretched first and second elastic materials to the first and second substrate layers, and subsequently allowing the first and second elastic materials of the layered elastic substrate to consolidate. The consolidated layered elastic substrate may be cut into discrete waistbands and joined to an advancing continuous length of absorbent articles. The continuous length of absorbent articles may be cut into individual absorbent articles having a first and a second waistband. As a result of joining the consolidated discrete waistband to the continuous length of absorbent articles at the reduced elongation, the gathers remain in the discrete waistband. Having a waistband with gathers may improve the actual and/or perceived fit of the absorbent article on a wearer.

It is to be appreciated that the layered elastic substrate can be formed in various ways. In some exemplary configurations, the first continuous substrate layer may be formed from a first continuous substrate, and the second continuous substrate layer may be formed from a second continuous substrate. In other exemplary configurations, the first continuous substrate layer and/or the second continuous substrate layer may be formed by folding a portion of a single continuous substrate onto another portion of the single continuous substrate.

Although the methods and apparatuses herein are discussed below in the context of manufacturing discrete elastic waistbands for diapers, it is to be appreciated that the methods and apparatuses herein can be applied to other elastic components used on diapers as well as other types of absorbent articles. Other elastic components used on an absorbent article may include, for example, ears or side panels, leg cuffs, topsheets, and backsheets.

The processes and apparatuses discussed herein may be used to assemble layered elastic substrates with various configurations, some of which may be used in the manufacture of different types of absorbent articles. To help provide additional context to the subsequent discussion, the following provides a general description of absorbent articles in the form of diapers that include layered elastic substrates in the form of elastic waistbands that may be assembled in accordance with the methods and apparatuses disclosed herein.

For the purposes of a specific illustration, FIG. 1 shows one example of a disposable absorbent article 150 in the form of a diaper 152 that may be constructed according to the methods and apparatuses disclosed herein. In particular, FIG. 1 is a plan view of one embodiment of a diaper 152 including a chassis 154 shown in a flat, unfolded condition, with the portion of the diaper 152 that faces a wearer oriented towards the viewer. A portion of the chassis structure is cut-away in FIG. 1 to more clearly show the construction of and various features that may be included in embodiments of the diaper.

As shown in FIG. 1, the diaper 152 includes a chassis 154 having a first ear 156, a second ear 158, a third ear 160, and a fourth ear 162. To provide a frame of reference for the present discussion, the chassis is shown with a longitudinal axis 164 and a lateral axis 166. The chassis 154 is shown as having a first waist region 168, a second waist region 170, and a crotch region 172 disposed intermediate the first and second waist regions 168 and 170. The periphery of the diaper 152 is defined by a pair of longitudinally extending side edges 174, 176; a first outer edge 178 extending laterally adjacent the first waist region 168; and a second outer edge 180 extending laterally adjacent the second waist region 170. As shown in FIG. 1, the chassis 154 includes an inner, body-facing surface 182, and an outer, garment-facing surface 184. As shown in FIG. 1, the chassis 154 of the diaper 152 may include an outer covering layer 186 including a topsheet 188 and a backsheet 190. An absorbent core 192 may be disposed between a portion of the topsheet 188 and the backsheet 190. As discussed in more detail below, one or more of the regions may be stretchable and may include an elastomeric material or layered elastic substrate as described herein. As such, the diaper 152 may be configured to adapt to a specific wearer's anatomy upon application and to maintain coordination with the wearer's anatomy during wear. As shown in FIG. 1, the diaper 152 may include leg cuffs 196 that may provide improved containment of liquids and other body exudates.

Although the first and second ears 156, 158 as well as the third and fourth ears 160, 162 shown in FIG. 1 are illustrated as being integrally formed with the chassis 154, it is to be appreciated that other embodiments may include ears that are discrete elements connected with the chassis. In some embodiments, the ears are configured to be stretchable. The ears may also include one or more fastener elements adapted to releasably connect with each other and/or other fastener elements on the chassis.

The diaper may be provided in the form of a pant-type diaper or may alternatively be provided with a re-closable fastening system, which may include fastener elements in various locations to help secure the diaper in position on the wearer. For example, fastener elements may be located on the first and second ears and may be adapted to releasably connect with one or more corresponding fastening elements located in the second waist region. It is to be appreciated that various types of fastening elements may be used with the diaper.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one exemplary configuration, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

As discussed above, the absorbent article 150 may also include a first discrete length of layered elastic substrate 194a and a second discrete length of layered elastic substrate 194b such as shown in FIG. 1 in the form of first and second waistbands 114a and 114b. The first and second waistbands 114a and 114b may provide improved fit and waste containment. The first waistband 114a may be located in the first waist region 168 and the second waistband 114b may be located in the second waist region 170. The first and second waistbands 114a and 114b may be configured to elastically expand and contract to dynamically fit the wearer's waist. The first and second waistbands 114a and 114b can be incorporated into the diaper 152 in accordance with the methods discussed herein and may be positioned at least longitudinally outwardly from the absorbent core 192 and generally form at least a portion of the first and/or second outer edges 178, 180 of the diaper 152. In addition, the first and second waistbands 114a and 114b may extend laterally to include the ears. The first and second waistbands 114 may be disposed on the outer, garment-facing surface 184 of the chassis 154; the inner, body-facing surface 182; or between the inner and outer facing surfaces. It is to be appreciated that the first waistband 114a and the second waistband 114b shown in FIG. 1 may comprise different materials and/or may be configured in different ways. The waistbands 114 may be constructed in a number of different configurations including those described in U.S. Patent Publication Nos. 2007/0142806; 2007/0142798; 2007/0287983; and 2012/0330263.

Figure 2E:
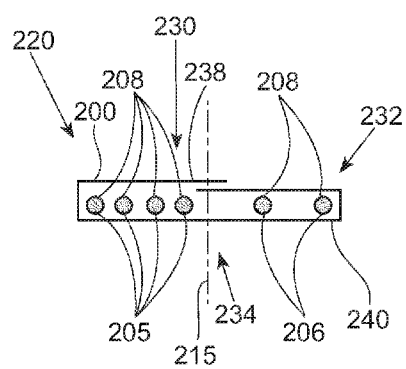
FIG. 2E is a schematic, sectional view of a continuous length of layered elastic substrate having elastic strands.

The first and second waistbands 114a and 114b of FIG. 1 may be formed from a continuous length of layered elastic substrate. As discussed in more detail below and as shown in FIG. 2A-2F, the layered elastic substrate 220 may be cut along cut line 215 to form the first waistband 114a and the second waistband 114b shown in FIG. 1. With reference to FIG. 2A, the layered elastic substrate 220 may include a first substrate layer 238 and a second substrate layer 240 separated by first and second elastic materials 205 and 206 to form a layered elastic substrate 220. In some exemplary configurations, the first substrate layer 238 may be formed from a first continuous substrate 202 and the second substrate layer 240 may be formed from a second continuous substrate 204 such as shown in FIG. 2A. The first and second elastic materials 205 and 206 may be in the form of elastic strands 208 such as shown in FIGS. 2A-2F. The first substrate 202 may be defined by a first surface 222 and an opposing second surface 224. The second substrate 204 may be defined by a first surface 226 and an opposing second surface 228. The elastic material 206 may be located between the first surface 222 of the first substrate 202 and the first surface 226 of the second substrate 204.

Figure 2F:
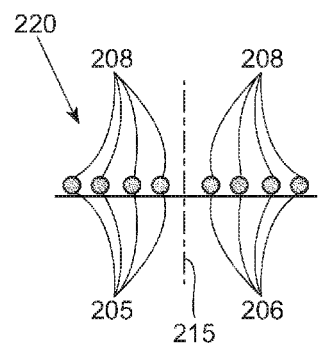
FIG. 2F is a schematic, sectional view of a continuous length of layered elastic substrate having elastic strands.
Figure 2G:
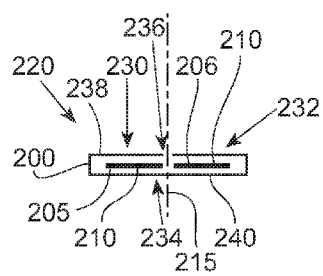
FIG. 2G is a schematic, sectional view of a continuous length of layered elastic substrate having elastic ribbons.
Figure 2I:
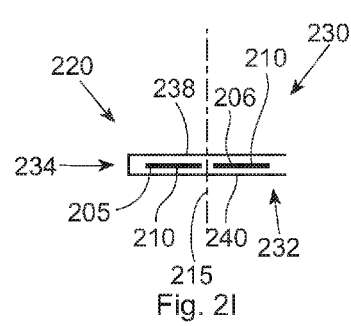
FIG. 2I is a schematic, sectional view of a continuous length of layered elastic substrate having elastic ribbons.
Figure 2H:
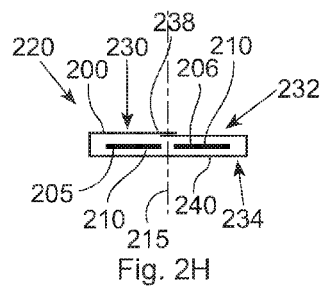
FIG. 2H is a schematic, sectional view of a continuous length of layered elastic substrate having elastic ribbons.
Figure 2J:
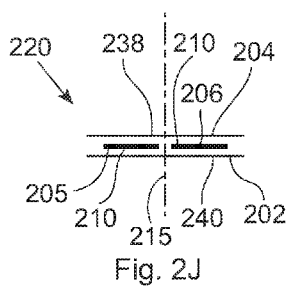
FIG. 2J is a schematic, sectional view of a continuous length of layered elastic substrate having elastic ribbons.

In some exemplary configurations, the first substrate layer 238 and/or the second substrate layer 240 of the layered elastic substrate 220 may be formed by folding a single continuous substrate 200 such as shown in FIGS. 2B-2E. The single continuous substrate 200 may be defined by a first edge region 230 and a second edge region 232 separated by a inner region 234, as well a first surface 216 and an opposing second surface 218. The first edge region 230 of the single continuous substrate 200 may be folded onto the second edge region 232 of the single continuous substrate 200 to form the first substrate layer 238 and the second substrate layer 240 as shown in FIG. 2C. In some exemplary configurations, the single continuous substrate 200 may be folded such that the first edge region 230 is proximate to the second edge region 232 so as to define a gap 236 between the first edge region 230 and the second edge region 232 such as shown in FIG. 2D. In some configurations, the first edge region 230 may abut the second edge region 232. In yet other exemplary configurations, the single continuous substrate 200 may be folded such that the first edge region 230 and the second edge region 232 overlap such as shown in FIG. 2E. It is to be appreciated that the single continuous substrate 200 may be folded in various ways. As shown in FIG. 2F, in some exemplary configurations the layered elastic substrate 220 may include a first substrate layer 238 formed from a single continuous substrate 200. It is to be appreciated that the first and/or second substrates 202 and 204 shown in FIG. 2A may also be folded into various configurations.

As shown in FIGS. 2A-2J, the first and second elastic materials 205 and 206 may be in the form of elastic strands 208, ribbons 210, or combinations thereof. While it is shown in FIGS. 2A-2C that the layered elastic substrate 220 may include eight elastic strands 208, it is to be appreciated that the layered elastic substrate 220 may include various numbers of elastic strands 208. In some exemplary configurations, the layered elastic substrate 220 may include one or more elastic ribbons 210 such as shown in FIGS. 2G-2J. It is to be appreciated that the elastic ribbons 210 may be formed from an elastic film. The first and second elastic materials 206 and 208 may have a mass density in the range of about 480 decitex to about 1580 decitex. In some exemplary configurations, a layered elastic substrate 220 may comprise elastic materials 206 of various mass densities. The elastic strands 208 may have various diameters and cross-sectional geometries. Exemplary elastic strands have a mass-density of 680 decitex and are manufactured by Hyousong of Seoul, Korea. Other exemplary elastic strands have a mass density of 680 decitex and are manufactured by Invista of Wichita, Kans. under the designation Lycra®.

It is to be appreciated that the first elastic material 205 may be configured differently than the second elastic material 206. For example, the first elastic material 205 may include a different number of elastic strands 208 or elastic ribbons 210 than the second elastic material 206 such as shown in FIGS. 2D and 2E. In some exemplary configurations, the first elastic material 205 may have a different mass density than the second elastic material 206. In some exemplary configurations, the first elastic material 205 may include elastic strands 208 of a different diameter than the elastic strands 208 of the second elastic material 206. It is to be appreciated that the first elastic material 205 may be configured in various ways and the second elastic material 206 may be configured in various ways.

In some exemplary configurations, the elastic strands 208 and/or ribbons 210 of the first and/or second elastic materials 205, 206 may be longitudinally spaced at constant intervals. In other exemplary configurations, the elastic strands 208 and/or ribbons 210 of the first and/or second elastic materials 205, 206 may be longitudinally spaced at different intervals. It is to be appreciated that the elastic strands 208 or the elastic ribbons 210 of the first elastic material 205 may be spaced at different intervals than the elastic strands 208 or the elastic ribbons 210 of the second elastic material 206.

It is to be appreciated that the layered elastic substrate may include various materials. For example, with respect to FIG. 2A, the first and/or second substrate layer 238 and 240 may include woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some exemplary configurations, the first and/or the second substrate layers 238 and 240 may include a polymeric film (e.g., polyethylene or polypropylene). In some exemplary configurations, the first and/or second substrate layers 238 and 240 may include a stretchable material. Exemplary nonwoven webs include spunbond-meltblown-meltblown-spunbond (SMMS) nonwovens having a basis weight of 10 grams per square meter (gsm) and spunbond-meltblown-spunbond (SMS) nonwovens having a basis weight of 10 gsm, both of which are manufactured by Avgol Ltd. of Tel Aviv, Israel. Other exemplary nonwoven webs include spunbond-meltblown-meltblown-meltblown-spunbond (SMMMS) nonwovens having a basis weight of 11 gsm, which is manufactured by Fibertex Nonwovens A/S of Aalborg, Denmark.

Figure 3B:
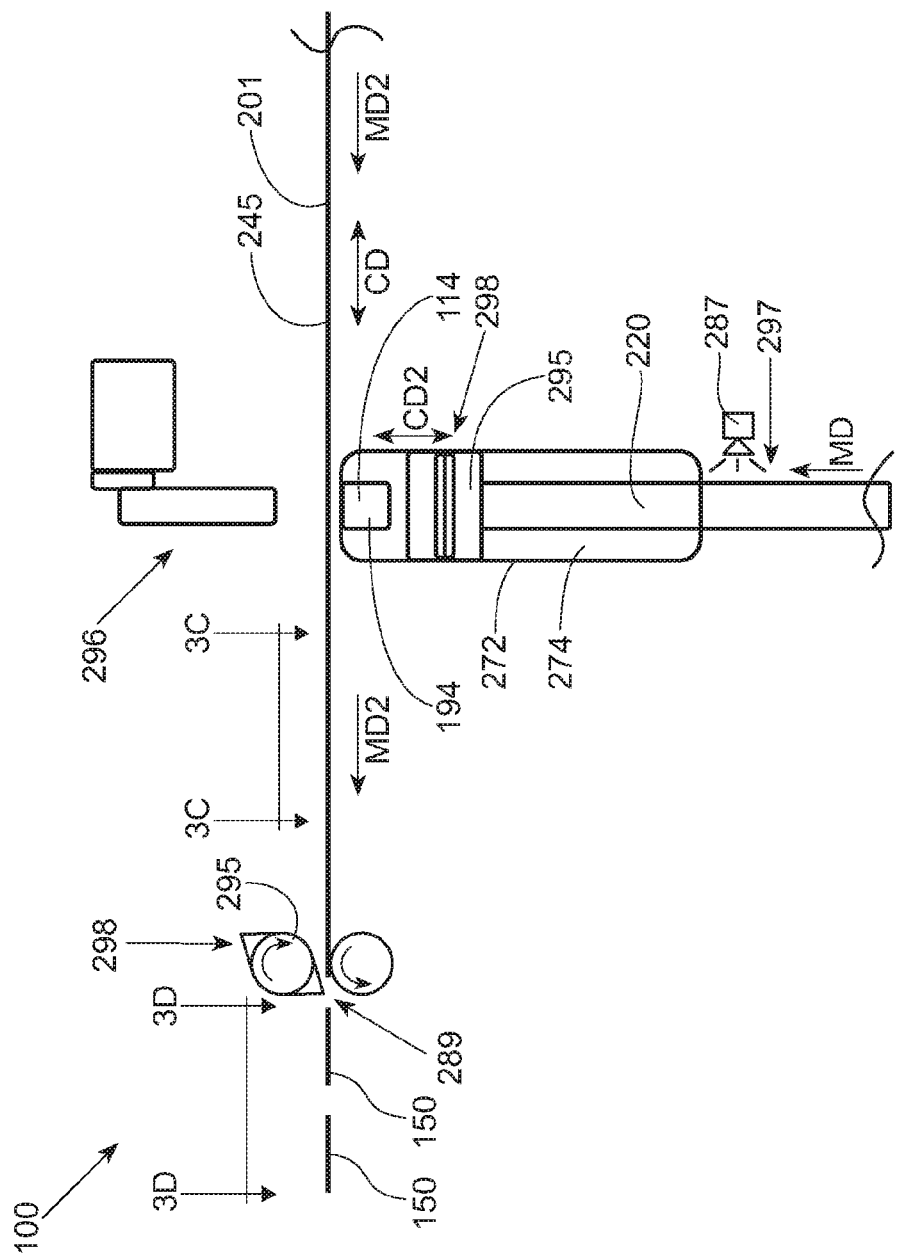
FIG. 3B is a schematic, side elevation view of the converting apparatus of FIG. 3A taken along lines 3B-3B.

As discussed above, the apparatuses and methods according to the present disclosure may be utilized to assemble discrete lengths of layered elastic substrate in the form of elastic waistbands for absorbent articles. It is to be appreciated that various apparatuses and methods may be used to assemble discrete lengths of layered elastic substrate. For example, FIGS. 3A and 3B show a converting apparatus 100 for assembling discrete lengths of layered elastic substrate in the form of waistbands for absorbent articles. It is to be appreciated that FIG. 3B is a view taken along line 3B-3B of FIG. 3A. Although the following description is provided in the context of the discrete absorbent article 150, it is to be appreciated that various absorbent articles can be manufactured according the methods disclosed herein, such as, the absorbent articles disclosed in U.S. Patent Application No. 61/499,294; U.S. Pat. Nos. 7,569,039 and 5,745,922; U.S. Patent Publication Nos. 2005/0107764A1; 2012/0061016A1; and 2012/0061015A1.

As shown in FIG. 3A, the converting apparatus 100 may be used to join a first continuous length of elastic material 205 and a second continuous length of elastic material 206 with continuous lengths of a first and second substrate 202 and 204 to form a layered elastic substrate 220. The layered elastic substrate 220 may advance onto a drum 272 to be cut into discrete lengths of layered elastic substrate 194, shown in the form of discrete waistbands 114. As shown in FIG. 3B, a continuous length of web material 245, shown in FIG. 3B as a continuous length of absorbent articles 201, may advance in a second machine direction MD2 and the discrete waistbands 114 may advance in the machine direction MD, which is also labeled as a second cross direction CD2 relative to the second machine direction MD2 of the advancing continuous length of absorbent articles 201. The elastic waistbands 114 may be intermittently bonded to the continuous length of absorbent articles 201 such that the elastic waistbands 114 are spaced apart on the continuous length of absorbent articles 201 in the second machine direction MD2.

The continuous length of absorbent articles 201 may be combined with other components upstream or downstream of combining the discrete waistbands 114 with the absorbent articles 201. It is to be appreciated that the continuous length of absorbent articles 201 may include various materials. For example, the continuous length of absorbent articles 201 may include topsheet material, backsheet material, or combinations thereof. The continuous length of absorbent articles 201 may be subjected to a final cut to create discrete absorbent articles 150 having a first waistband with the first elastic material and a second waistband with the second elastic material. An exemplary process for attaching elastic components to absorbent articles is described in U.S. Provisional Patent Application No. 61/665,930.

As shown in FIG. 3A, the continuous length of first elastic material 205 is advanced in a in the machine direction MD in a stretched state to a first metering device 250 and the continuous length of second elastic material 206 is advanced in the machine direction MD in a stretched state to a second metering device 252. The continuous lengths of first and second substrates 202 and 204 are advanced in the machine direction MD to a third metering device 254. The first elastic material 205 and the second elastic material 206 are advanced in the machine direction MD and combined with the first and second substrates 202 and 204 at the third metering device 254 to form a continuous layered elastic substrate 220. The first elastic material 205 may be stretched to a first elongation between the first and third metering devices 250 and 254. The second elastic material 206 may be stretched to a second elongation between the second and third metering devices 252 and 254. It is to be appreciated that the first elongation may be greater than the second elongation. As shown in FIG.

3A, adhesive 297 may be applied to the first substrate 202, the second substrate 204, and the first and second elastic materials 205 and 206 using an adhesive applicator 287 before advancing through the third metering device 254. From the third metering device 254, the layered elastic substrate 220 may advance in the machine direction MD to a fourth metering device 255. The layered elastic substrate 220 may be consolidated between the third and fourth metering devices 254 and 255.

It is to be appreciated that the first elastic material and the second elastic material may be configured to provide different amounts of contraction to the first and second waistbands in various ways. In some exemplary configurations, the contraction of the first and second elastic materials may be dependent upon various factors, including the number of elastic strands or ribbons in the first and second layered elastic substrates, the mass density of the elastic material; and the percent elongation of the strands, ribbons, or films in the first and second layered elastic substrates. For example, a first elastic material may be stretched to a first elongation that is greater than a second elongation of the second elastic material. In such an exemplary configuration, a first elastic waistband comprising the first elastic material may have a greater contraction that a second elastic waistband comprising the second elastic material. In some exemplary configurations, a first elastic material may have a higher mass density than a second elastic material. As a result, in such an exemplary configuration, a first waistband comprising the first elastic material may have a greater contraction than a second waistband comprising the second waistband. In some exemplary configurations, a first elastic material may include a greater number of elastic strands or ribbons than a second elastic material. In such an exemplary configuration, a first waistband comprising the first elastic material may have a greater contraction than a second waistband comprising the second elastic material.

It is to be appreciated that the metering devices may be configured in various ways. For example, the first metering device 250 shown in FIG. 3A includes a roller 256 having an outer circumferential surface 260 and rotates about an axis of rotation 276. The roller 256 rotates such that the outer circumferential surface 260 has a surface speed V1. The second metering device 252 shown in FIG. 3A includes a roller 258 having an outer circumferential surface 262 and rotates about an axis of rotation 278. The roller 258 rotates such that the outer circumferential surface 262 has a surface speed V2. It is to be appreciated that V2 may be greater than V1. The third metering device 254 shown in FIG. 3A includes a first roller 264 having an outer circumferential surface 268 and rotates about a first axis of rotation 280 and a second roller 266 having an outer circumferential surface 270 and rotates about a second axis of rotation 282. The first roller 264 and the second roller 266 rotate in opposite directions, and the second roller 266 is adjacent the first roller 264 to define a first nip 286 between the first roller 264 and the second roller 266. The first and second rollers 264 and 266 rotate such that the outer circumferential surfaces 268 and 270 have a surface speed V3. It is to be appreciated that V3 may be greater than speeds, V2 and V1. The fourth metering device 255 shown in FIG. 3A includes a drum 272 having an outer circumferential surface 274 and rotates about a third axis of rotation 284. The drum 272 rotates such that the outer circumferential surface 274 has a surface speed V4. It is to be appreciated that V4 may be less than V3, and V4 may be greater than V1 and V2.

With continuing reference to FIG. 3A, upstream of the first metering device 250, the first elastic material 205 may advance at a surface speed V1 or less. The first elastic material 205 stretches to the first elongation between the first metering device 250 and the third metering device 254 because the first elastic material 205 advances at surface speed V1 at the outer circumferential surface 260 of the roller 256 of the first metering device 250 and at surface speed V3 at the first nip 286 of the third metering device 254, wherein V3 is greater than V1. Similarly, upstream of the second metering device 252, the second elastic material 206 may advance at a surface speed V2 or less. The second elastic material 206 stretches to the second elongation between the second metering device 252 and the third metering device 254 because the second elastic material 206 advances at surface speed V2 at the outer circumferential surface 262 of the roller 258 of the second metering device 252 and at surface speed V3 at the first nip 286 of the third metering device 254, wherein V3 is greater than V2. Likewise, since V2 is greater than V1, and V3 is greater than V1 and V2, the first elastic material 205 stretches to a first elongation that is greater than the second elongation of the second elastic material 206.

As shown in FIG. 3A, the layered elastic substrate 220 consolidates to a reduced elongation between the third metering device 254 and the fourth metering device 255 because the layered elastic substrate 220 advances at surface speed V3 at the first nip 286 and advances at surface speed V4 at the drum 272, wherein V4 is greater than V1 and V2, and V4 is less than V3. At the same time, the first elastic material 205 consolidates in the machine direction MD from the first elongation to a third elongation that is less than the first elongation, and the second elastic material 206 consolidates in the machine direction MD from the second elongation to a fourth elongation that is less than the second elongation. As a result of consolidating the layered elastic substrate 220, gathers form in the layered elastic substrate 220 between the third and fourth metering devices 254 and 255 as shown in FIG. 3A. It is to be appreciated that the third elongation of the first elastic material 205 may be greater than the fourth elongation of the second elastic material 206.

It is to be appreciated that various other apparatuses may be used for the metering devices. For example, the metering devices may include rollers, drums, conveyors, and combinations thereof. The metering devices may include one roller, drum, or conveyor. In some exemplary configurations, the first and second metering devices may include more than one roller, drum, conveyor, or combinations thereof.

With continuing reference to FIG. 3A, the metering devices may be configured to stretch the first and second elastic materials 205 and 206 and/or to consolidate the first and second elastic materials 205 and/or 206 of the layered elastic substrate 220. In particular, the first and third metering devices 250 and 254 may be configured to stretch the first elastic material 205 to a first elongation. The second and third metering devices 252 and 254 may be configured to stretch the second elastic material 206 to the second elongation. The first elongation may be 150% and the second elongation may be 100%. In addition, the third metering device 254 and the fourth metering devices 255 may be configured to consolidate the layered elastic substrate 220 such that the first elastic material 205 consolidates from the first elongation to the third elongation and the second elastic material 206 consolidates from the second elongation to the fourth elongation. The third elongation may be 80% and the fourth elongation may be 20%.

It is to be appreciated that the methods and apparatuses disclosed herein may be configured to stretch the first elastic material 205 to a first elongation of various percentages and the second elastic material 206 to a second elongation of various percentages. For example, the first elongation may be about 110%, 120%, 130%, 140%, 150%, 160%, 170%, 180%, 190%, or 200% and the second elongation may be about 100%, 110%, 120%, 130%, 140%, 150%, 160%, 170%, 180%, 190%, or 200%. The first elongation of the first elastic material 205 may be greater than the second elongation of the second elastic material 206. Also, it is to be appreciated that the methods and apparatus disclosed herein may be configured to consolidate the first elastic material 205 to a third elongation of various percentages and the second elastic material 206 to a fourth elongation of various percentages. For example, the third elongation may be about 10%, 20%, 30%, 40%, 50%, 60%, 70%, 80%, 90%, 100%, 110%, 120%, 130%, 140%, or 150% and the fourth elongation may be about 10%, 20%, 30%, 40%, 50%, 60%, 70%, 80%, 90%, 100%, 110%, 120%, 130%, 140%, or 150%. It is to be appreciated that the third elongation of the first elastic material 205 may be greater than the fourth elongation of the second elastic material 206.

Referring to FIGS. 3A and 3B, the layered elastic substrate 220 may be cut into discrete waistbands 114 and joined with an advancing continuous length of absorbent articles 201 advancing in the second machine direction MD2. The continuous length of layered elastic substrate 220 may advance onto and partially wrap around the outer circumferential surface 274 of the drum 272. A cutter 298, shown in FIGS. 3A and 3B as a knife roll 295 for purposes of illustration, may be positioned adjacent to the outer circumferential surface 274 of the drum 272 to cut the layered elastic substrate 220 into discrete waistbands 114. As discussed in more detail below, the drum 272 may be configured with a vacuum system to hold the discrete waistbands 114 in a stretched state on the outer circumferential surface 274 of the drum 272 after being cut from the continuous layered elastic substrate 220.

Figure 4:
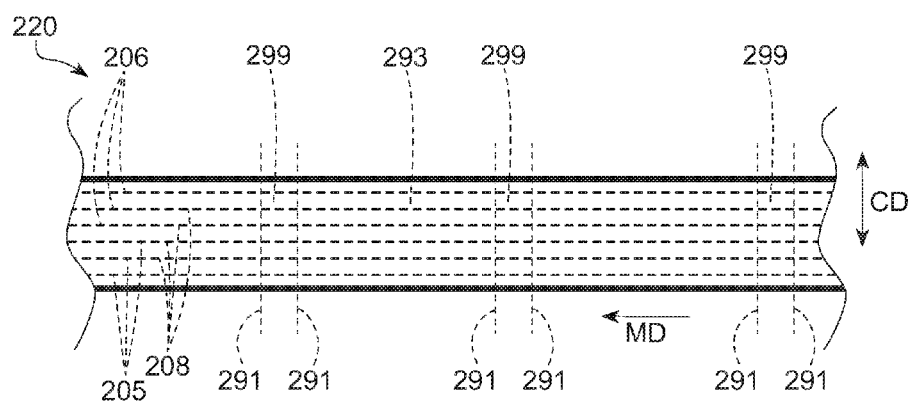
FIG. 4 is schematic, plan view of a continuous length of layered elastic substrate including an elastic material intermittently bonded to first and second substrate layers taken along line 4-4 of FIG. 3A.
Figures 5A, 5B:
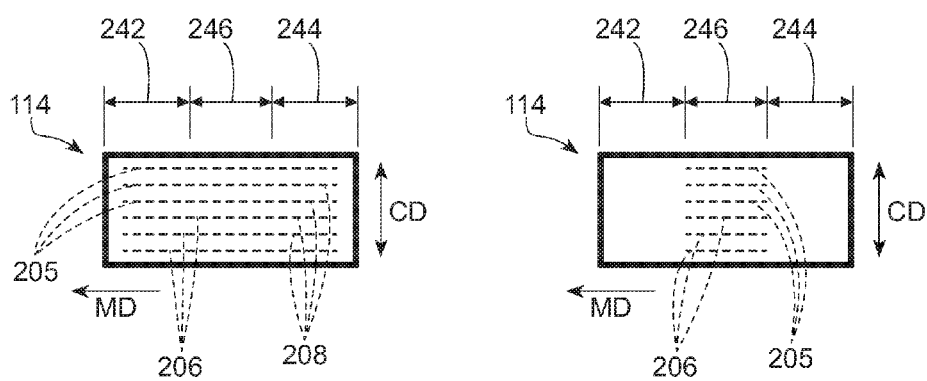
FIG. 5A is a schematic, plan view of a discrete length of layered elastic substrate having elastic material intermittently bonded to first and second substrate layers.
FIG. 5B is a schematic, plan view of a discrete length of layered elastic substrate having elastic material intermittently bonded to first and second substrate layers.
Figure 6:
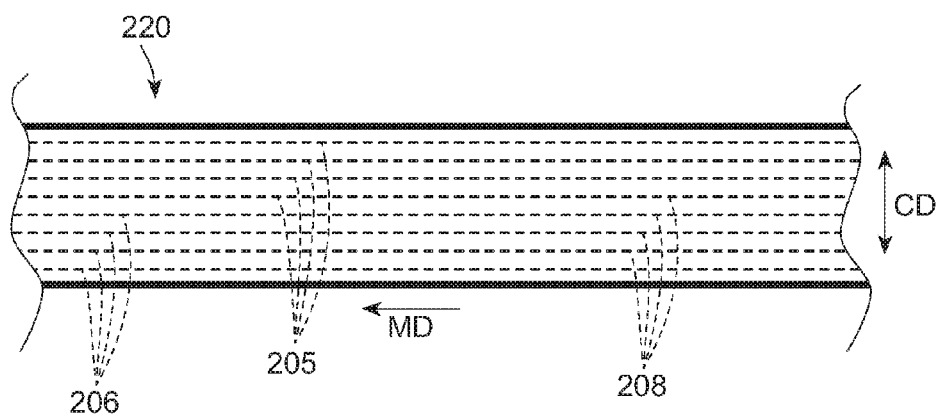
FIG. 6 is a schematic, plan view of a continuous length of layered elastic substrate having an elastic material continuously bonded to first and second substrates.
Figure 7:
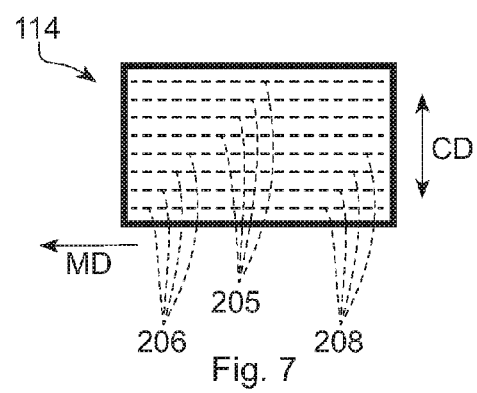
FIG. 7 is a schematic, plan view of a discrete length of layered elastic substrate having an elastic material continuously bonded to first and second substrate layers.

In some exemplary configurations, the elastic material may retract after the layered elastic substrate is cut into discrete lengths of layered elastic substrate. As shown in FIG. 4, the elastic strands 208 may be intermittently bonded to the first and second substrates layers, forming bonded regions 293 and nonbonded regions 299 in the layered elastic substrate 220. It is to be appreciated that FIG. 4 is a view taken along line 4-4 of FIG. 3A. With reference to FIGS. 3A, 3B, and 4, in such an exemplary configuration, the cutter 298 may be configured to cut the layered elastic substrate 220 at the nonbonded regions 299 shown in FIG. 4. Consequently, as shown in FIG. 5A, the severed ends of the elastic strands 208 retract back to the bonded regions 293 of the waistband 114. The waistband 114 may have a first end portion 242 and a second end portion 244 separated by a central portion 246 as shown in FIGS. 5A and 5B. With reference to FIGS. 4, 5A, and 5B, in some exemplary configurations, the elastic strands 208 may be intermittently bonded to the layered elastic substrate 220 such that the elastic strands 208 retracts back to the bonded regions 293 located in the central portion 246. In other exemplary configurations, the elastic strands 208 may be continuously bonded to the layered elastic substrate 220, such as shown in FIG. 6. In such an example, once the layered elastic substrate 220 is cut by the cutter 298 shown in FIGS. 3A and 3B, the elastic material will extend the entire length of the waistband 114 as shown in FIG. 7.

With reference back to FIGS. 3A and 3B, once the discrete waistbands 114 are cut from the layered elastic substrate 220, a tamper apparatus 296 may be used to bond the waistbands 114 to the continuous length of absorbent articles 201. Adhesive 297 may be applied to the discrete waistbands 114 using an adhesive applicator 287 before or while the waistbands 114 advance on the outer circumferential surface 274 of the drum 272. The tamper apparatus 296 may direct a portion of the continuous length of absorbent articles 201 into contact with the discrete waistband 114 advancing on the drum 272. Vacuum may be intermittently interrupted to the drum 272 to allow the discrete waistband 114 to release from the outer circumferential surface 274 of the drum 272. The discrete waistband 114 may bond to the continuous length of absorbent articles 201 in a stretched state. The tamper apparatus 296 may shift away from the drum 272 to allow the discrete waistband 114 to be removed from the drum 272. The continuous length of absorbent articles 201, including the discrete waistbands 114 advances in the second machine direction MD2 and subsequent discrete waistbands 114 are bonded to the continuous length of absorbent articles 201 such that discrete waistbands 114 are spaced apart from each other discrete waistband 114 in the second machine direction MD2 as shown in FIG. 3C. It is to be appreciated that FIG. 3C is a view taken along line 3C-3C of FIG. 3B. An exemplary tamper apparatus is described in U.S. Provisional Patent Application No. 61/665,928.

Figure 3D:
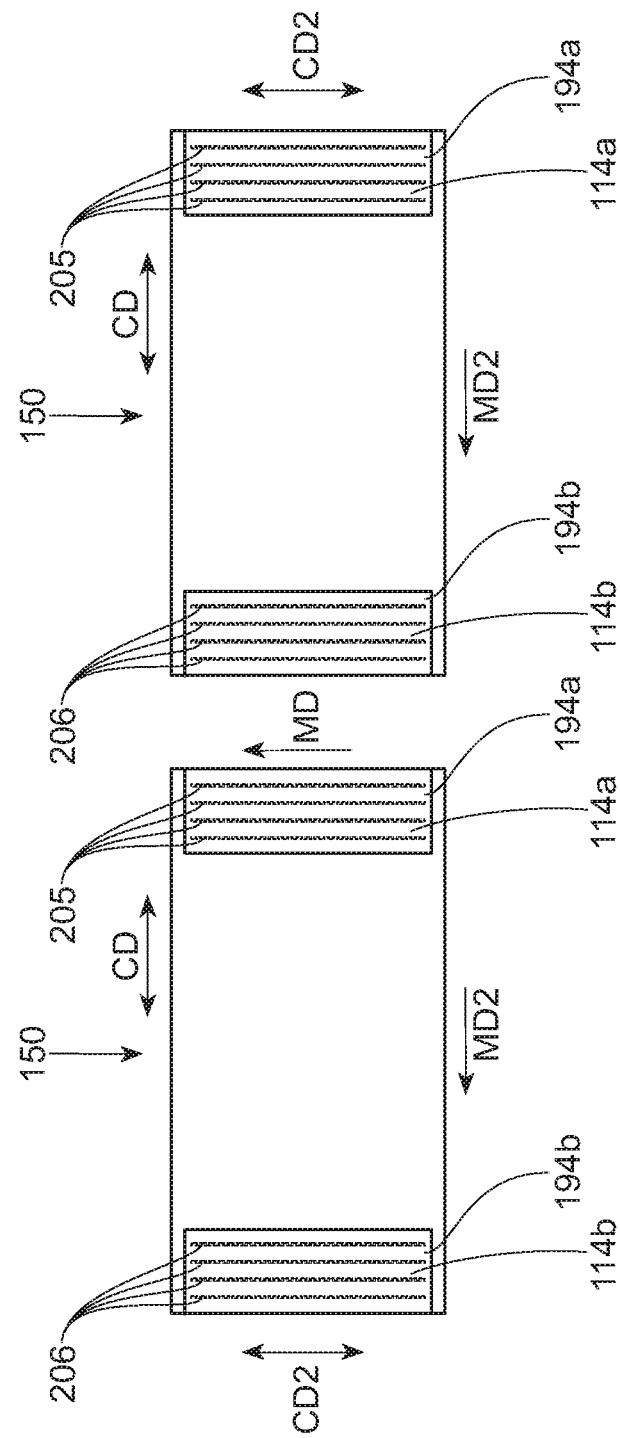
FIG. 3D is a schematic, plan view of a discrete absorbent article having two discrete elastic waistbands taken along line 3D-3D of FIG. 3B.

As shown in FIG. 3B, the absorbent articles 201 having waistbands 114 may be advanced in the second machine direction MD2 through a nip 289 to be cut by a rotating knife roll 295 in the cross direction CD into discrete absorbent articles 150. As shown in FIGS. 3C and 3D, the waistbands 114 may be defined by a first edge region 340 and a second edge region 342 separated by an inner region 344. The continuous length of absorbent articles 201 may be cut in the machine direction MD along the inner region 344 of the discrete waistbands 114, thereby forming a first waistband 114a on an absorbent article 150 and a second waistband 114b on a subsequently advancing absorbent article 150. In some exemplary configurations, the continuous length of absorbent articles 201 may be cut in the machine direction MD along a centerline 116 of the waistband 114. In other exemplary configurations, it is to be appreciated that the continuous length of absorbent articles may be cut away from the centerline 116 of the waistband 114. It is to be appreciated that FIG. 3D is a view taken along line 3D-3D of FIG. 3B.

As shown in FIG. 3C, the continuous length of absorbent articles 201 may be cut such that the first waistband 114a may include the first elastic material 205 and the second waistband 114b may include the second elastic material 206. As a result, the absorbent article 150 includes the first waistband 114a having the first elastic material 205 stretched to the third elongation and the second waistband 114b having the second elastic material 206 stretched to the fourth elongation, where the third elongation is greater than the fourth elongation. With reference to FIGS. 3E-3H, in some exemplary configurations, the continuous length of absorbent articles 201 may be cut adjacent to the waistband 114, either before or after the waistband 114, thereby creating an absorbent article 150 having only one waistband 114. It is to be appreciated that the absorbent articles may have waistbands arranged in various configurations.

Figure 8A:
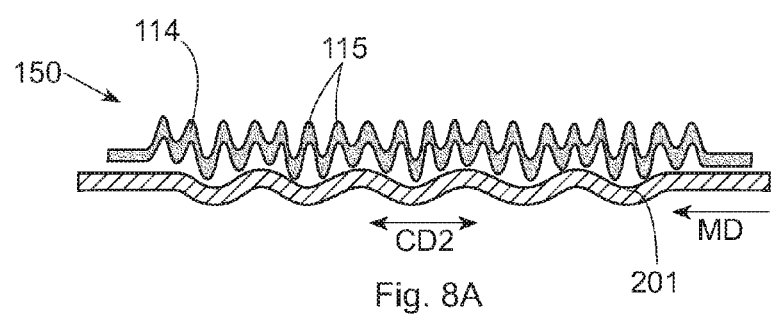
FIG. 8A is a sectional view of an absorbent article in a relaxed state and having a discrete elastic waistband.
Figure 8B:
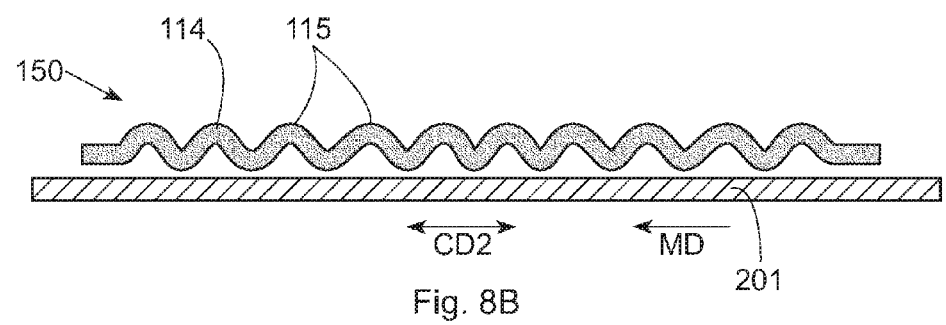
FIG. 8B is a sectional view of an absorbent article in a fully stretched state and having a discrete elastic waistband.

As a result of consolidating the layered elastic substrate and subsequently bonding the consolidated waistbands 114 to the absorbent articles 150 in a stretched state, gathers 115 form in the waistband 114 as shown in FIGS. 8A and 8B. FIG. 8A shows a waistband 114 having gathers 115 when the absorbent article 150 is relaxed and FIG. 8B shows a waistband 114 having gathers 115 when the absorbent article is fully stretched.

Figure 9:
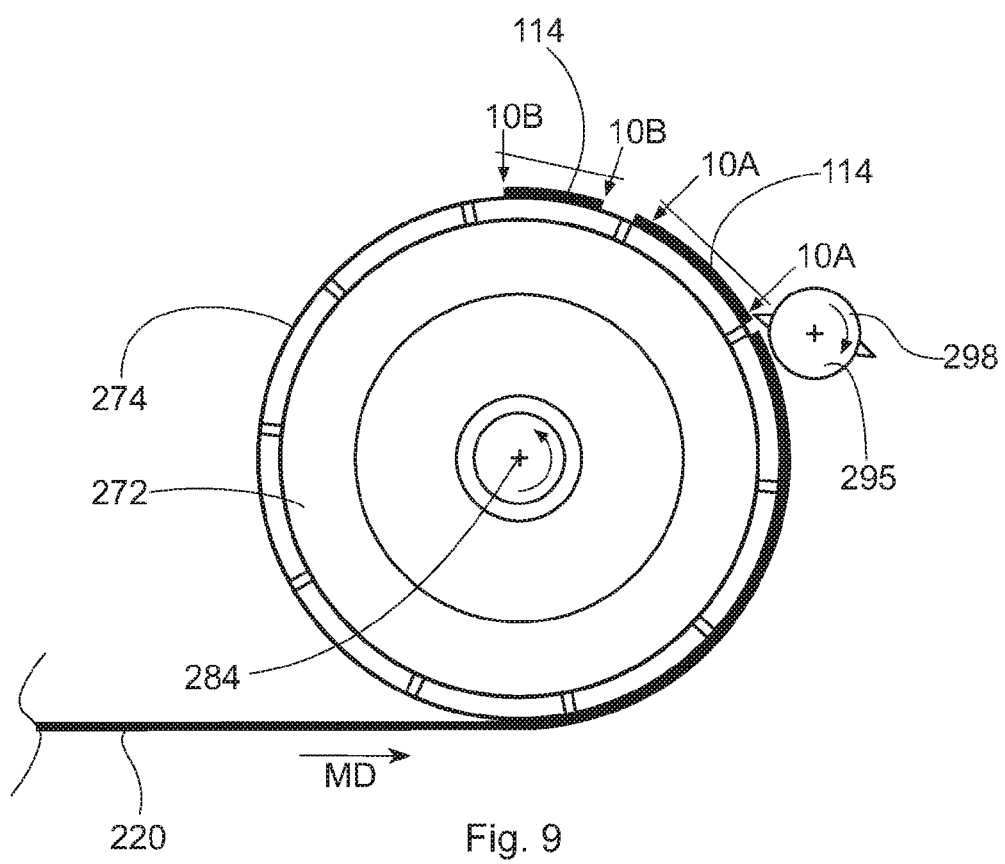
FIG. 9 is a schematic, side elevation view of a drum that is used to cut and consolidate a discrete length of layered elastic substrate.
Figure 10A:
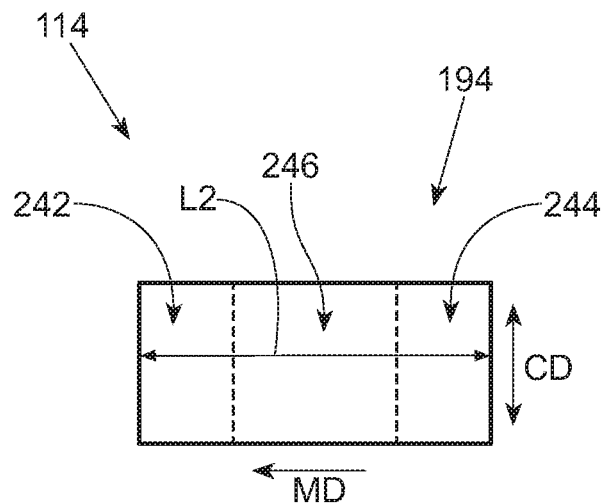
FIG. 10A is a schematic, plan view of a discrete waistband taken along line 10A-10A of FIG. 9.
Figure 10B:
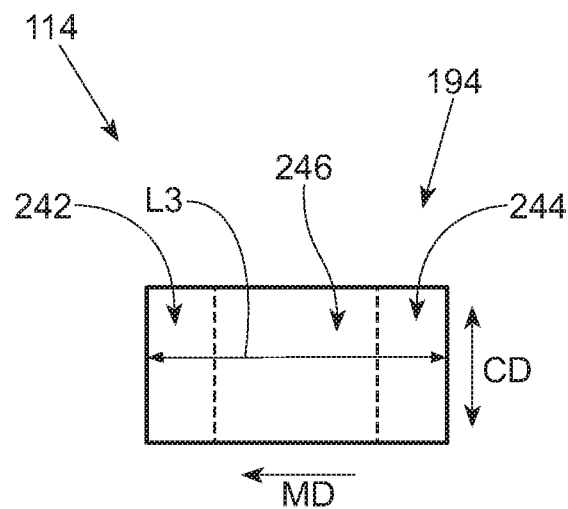
FIG. 10B is a schematic, plan view of a discrete waistband taken along line 10B-10B of FIG. 9.
Figure 10C:
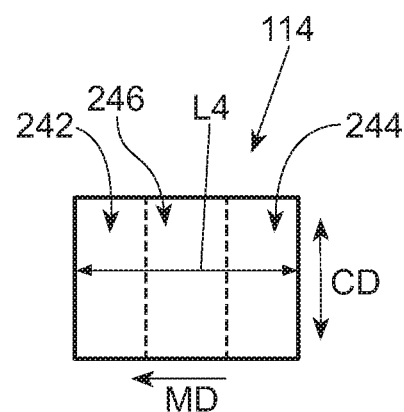
FIG. 10C is a schematic, plan view of a discrete waistband.
Figure 10D:
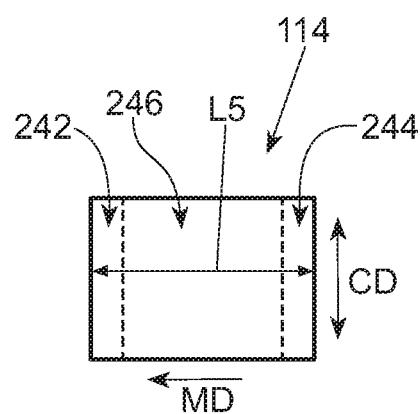
FIG. 10D is a schematic, plan view of a discrete waistband.

In some exemplary configurations, the discrete waistbands 114 may be further consolidated while advancing on the outer circumferential surface 274 of the drum 272 as shown in FIG. 9. With reference to FIGS. 9, 10A, and 10B, the waistbands 114 may have a first end portion 242 and a second end portion 244 separated by a central portion 246. In some exemplary configurations, the drum 272 may be configured to increase the vacuum pressure, and thus decrease the vacuum force, applied to the first and second end portions 242 and 244 of the waistband 114 such that the waistband consolidates from a second length L2 shown in FIG. 10A to a third length L3 as shown in FIG. 10B. It is to be appreciated that FIG. 10A is a view taken alone line 10A-10A of FIG. 9 and FIG. 10B is a view taken along line 10B-10B of FIG. 9. As shown in FIG. 10B, the central portion 246 may remained stretched while the first and second end portions 242 and 244 consolidate. In some exemplary configurations, the vacuum pressure applied to the first end portion 242, second end portion 244, and the central portion 246 of the discrete waistband 114 may be increased so that the first end portion 242, second end portion 244, and the central portion 246 consolidate. As a result, the waistband 114 consolidates from a second length L2 to a fourth length L4 shown in FIG. 10C. In other exemplary configurations, vacuum pressure applied to the first and second end portions 242 and 244 may be increased such that the first and second end portions 242 and 244 relax and the waistband consolidates from a second length L2 to a fifth length L5 as shown in FIG. 10D. Methods and apparatuses for consolidating elastic substrates are described in U.S. Provisional Patent Application No. 61/665,933.

Figure 11:
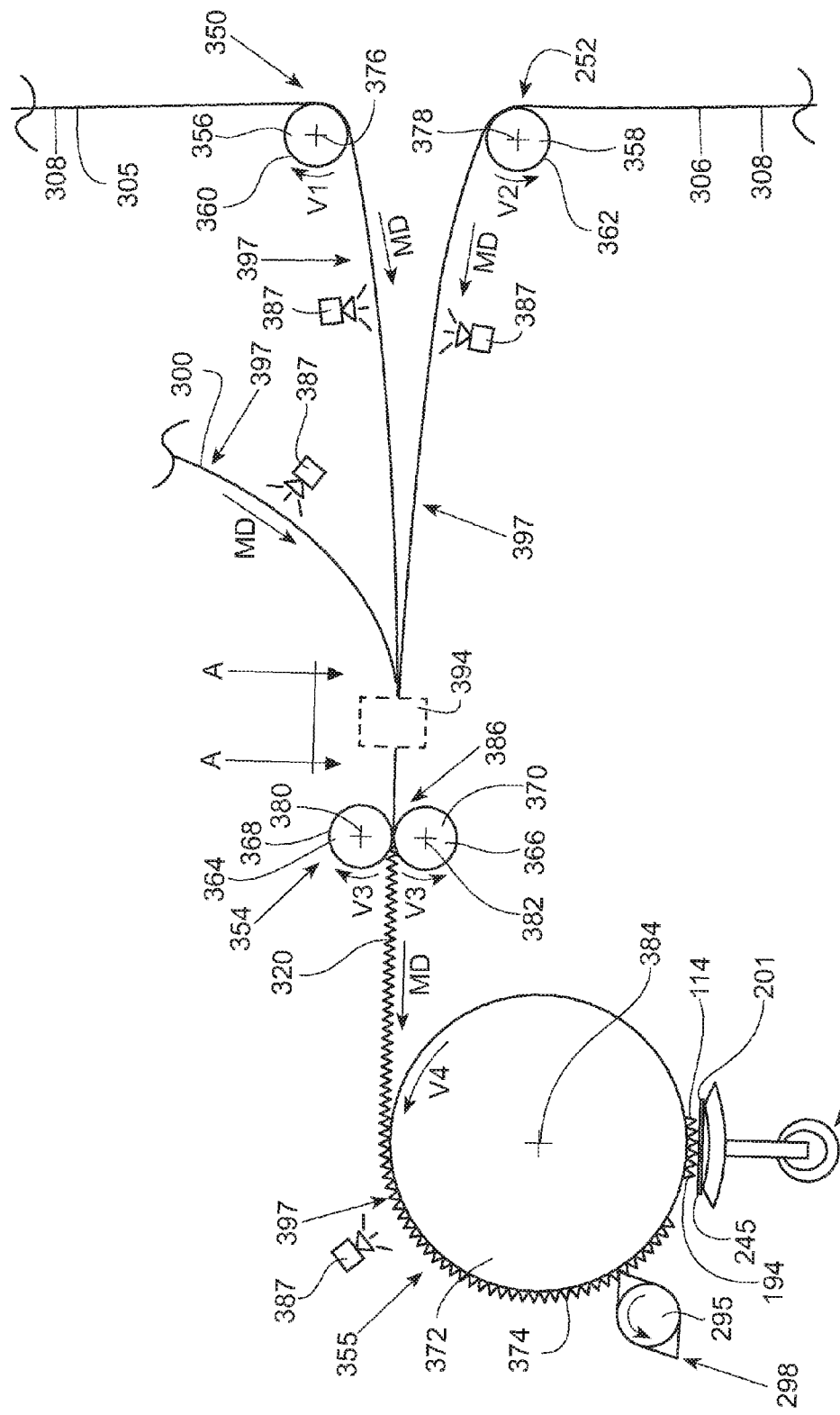
FIG. 11 is a schematic, side elevation view of a converting apparatus for making a layered elastic substrate in the form of discrete waistbands for absorbent articles.

It is to be appreciated that various methods and apparatuses may be used for making discrete lengths of layered elastic substrates. For example, FIG. 11 shows another exemplary converting apparatus 100 for assembling discrete lengths of layered elastic substrate. The continuous length of first elastic material 305 is advanced in a stretched state in the machine direction MD to a first metering device 350 and the continuous length of second elastic material 306 is advanced in a stretched state in the machine direction MD to a second metering device 352. A single continuous substrate 300 and the first and second elastic materials 305 and 306 are advanced in the machine direction MD to a folding apparatus 394. Adhesive 397 may be applied to the single continuous substrate 300, the first elastic material 305, and second elastic materials 306 using an adhesive applicator 387 before advancing to the folding apparatus 394. The folding apparatus 394 folds the single continuous substrate over the first elastic material 305 and the second elastic material 306. From the folding apparatus 394, the first elastic material 305, the second elastic material 306, and the single continuous substrate 300 advance to the third metering device 354. The first elastic material 305 and the second elastic material 306 are bonded to the single continuous substrate 300 at the third metering device 354 to form a continuous layered elastic substrate 320. The first elastic material 305 may be stretched to a first elongation between the first and third metering devices 350 and 354 and the second elastic material 306 may be stretched to a second elongation between the second and third metering devices 352 and 354. From the third metering device 354, the layered elastic substrate 320 may advance in the machine direction MD to a fourth metering device 355. The layered elastic substrate 320 may be consolidated between the third and fourth metering devices 354 and 355.

The first metering device 350 shown in FIG. 11 includes a roller 356 having an outer circumferential surface 360 and rotates about an axis of rotation 376. The roller 356 rotates such that the outer circumferential surface 360 has a surface speed V1. The second metering device 352 shown in FIG. 11 includes a roller 358 having an outer circumferential surface 362 and rotates about an axis of rotation 378. The roller 358 rotates such that the outer circumferential surface 362 has a surface speed V2, wherein V2 is greater than V1. The third metering device 354 shown in FIG. 11 includes a first roller 364 having an outer circumferential surface 368 and rotates about a first axis of rotation 380 and a second roller 366 having an outer circumferential surface 370 and rotates about a second axis of rotation 382. The first roller 364 and the second roller 366 rotate in opposite directions, and the second roller 366 is adjacent the first roller 364 to define a first nip 386 between the first roller 364 and the second roller 366. The first and second rollers 364 and 366 rotate such that the outer circumferential surfaces 368 and 370 have a surface speed V3, wherein V3 is greater than V1 and V2. The fourth metering device 355 shown in FIG. 11 includes a drum 372 having an outer circumferential surface 374 and rotates about a third axis of rotation 384. The drum 372 rotates such that the outer circumferential surface 374 has a surface speed V4, wherein V4 is less than V3, and V4 is greater than V1 and V2.

With continuing reference to FIG. 11, upstream of the first metering device 350, the first elastic material 305 may advance at a surface speed V1 or less. The first elastic material 305 stretches to the first elongation between the first metering device 350 and the third metering device 354 because the first elastic material 305 advances at surface speed V1 at the outer circumferential surface 360 of the roller 356 of the first metering device 350 and at surface speed V3 at the first nip 386 of the third metering device 354, wherein V3 is greater than V1. Similarly, upstream of the second metering device 352, the second elastic material 306 may advance at a surface speed V2 or less. The second elastic material 306 stretches to the second elongation between the second metering device 352 and the third metering device 354 because the second elastic material 306 advances at surface speed V2 at the outer circumferential surface 362 of the roller 358 of the second metering device 352 and at surface speed V3 at the first nip 386 of the third metering device 354, wherein V3 is greater than V2.

The layered elastic substrate 320 consolidates to a reduced elongation between the third metering device 354 and the fourth metering device 355 because the layered elastic substrate 320 advances at surface speed V3 at the first nip 386 of the third metering device 354 and advances at surface speed V4 at the outer circumferential surface 374 drum 372 of the fourth metering device 355, wherein V4 is greater than V2 and V1, but less than V3. At the same time, the first elastic material 305 consolidates in the machine direction MD from the first elongation to a second elongation that is less than the first elongation and the second elastic material 306 consolidates in the machine direction MD from the second elongation to a fourth elongation that is less than the second elongation. It is to be appreciated that the third elongation may be greater than the fourth elongation.

Figure 12:
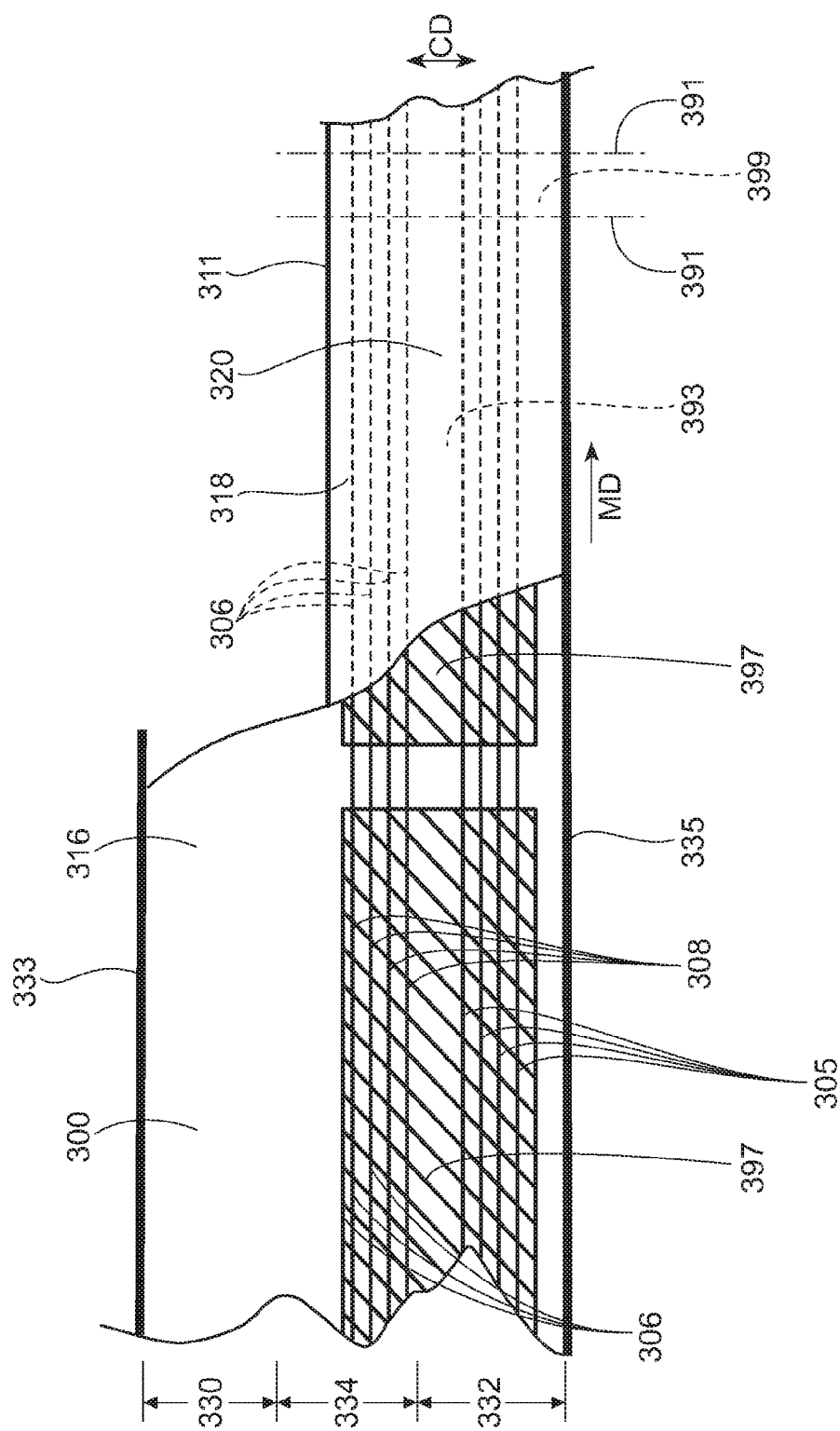
FIG. 12 is a schematic, plan view of a single continuous substrate and elastic material taken along line A-A from FIG. 11.
Figure 13:
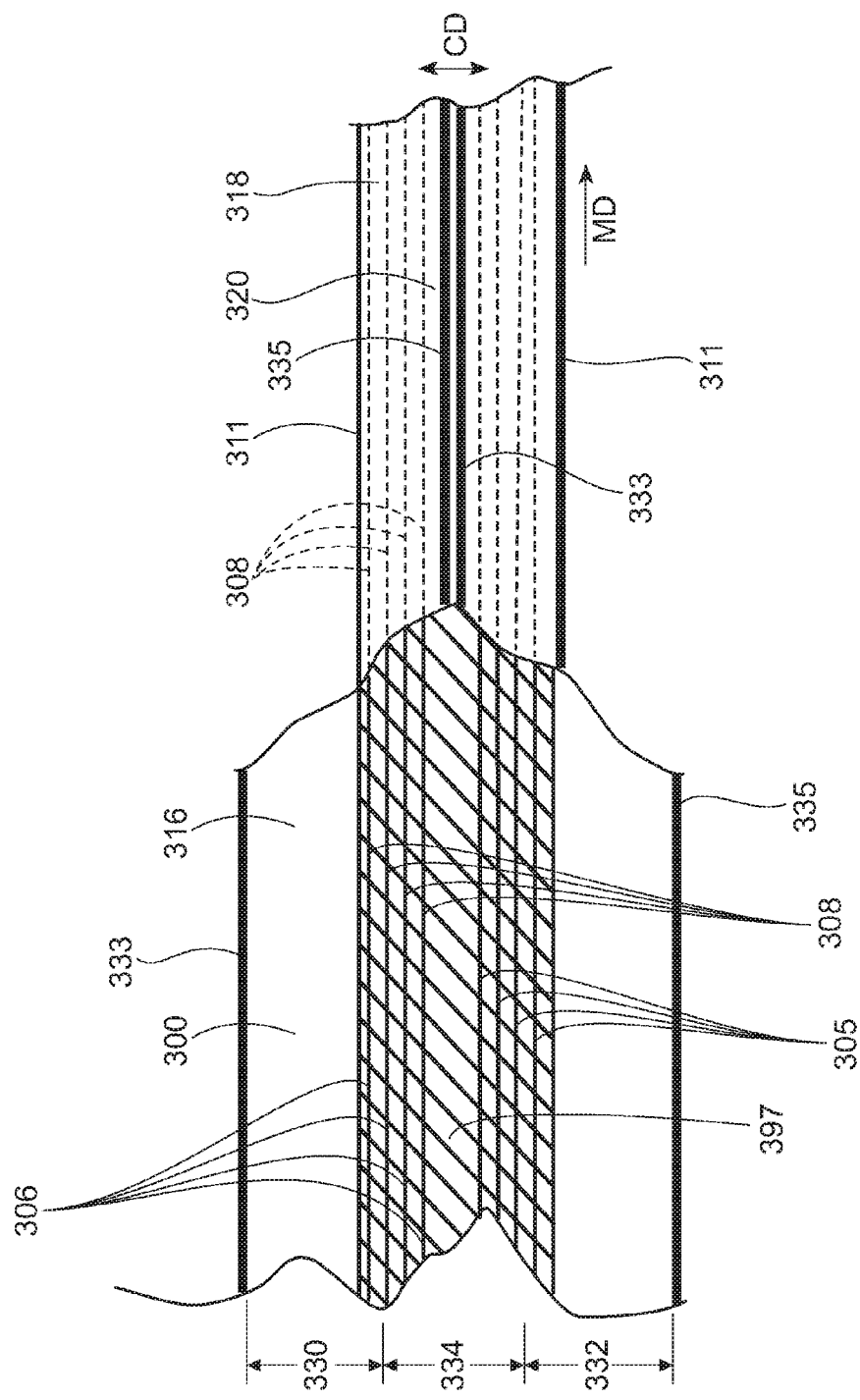
FIG. 13 is a schematic, plan view of a single continuous substrate and elastic material taken along line A-A from FIG. 11.

It is to be appreciated that the folding apparatus 394 of FIG. 11 may be configured to fold the single continuous substrate 300 in various ways. For example, FIGS. 12 and 13 show two exemplary folding configurations for the single continuous substrate 300 of FIG. 11. It is to be appreciated that FIGS. 12 and 13 are alternative views taken along line A-A of FIG. 11. As shown in FIGS. 12 and 13, the single continuous substrate 300 may include a first surface 316 and an opposing second surface 318. The single continuous substrate 300 may be defined by a first edge region 330 and second edge region 332 separated by an inner region 334. As shown in FIG. 12, in some exemplary configurations, the single continuous substrate 300 may be folded in the machine direction MD at a fold line 311 of the inner region 334 such that the first edge region 330 and the second edge region 332 are in a facing relationship.

In some exemplary configurations, as shown in FIG. 13, the single continuous substrate 300 may be folded at two fold lines 311 in each of the first and second edge regions 330 and 332 in the machine direction MD such that the first surface 316 of each of the first edge region 330 and the second edge region 332 are in a facing relationship with the first surface 316 of the inner region 334. FIG. 13 shows an exemplary configuration where the first and second lateral edges 333 and 335 are overlapping such that a portion of the first surface 316 of the second edge region 332 is in a facing relationship with a portion of the second surface 318 of the first edge region 330 and portions of the first surface 316 of the first and second edge regions 330 and 332 are in a facing relationship with the first surface 316 of the inner region 334. However, the first and second lateral edges 333 and 335 may be arranged in various configurations. For example, as shown in FIG. 2D, the single continuous substrate 300 may be folded such that the first lateral edge 333 is adjacent to the second lateral edge 335, and in some embodiments, the first lateral edge 333 may abut the second lateral edge 335.

With reference back to FIG. 12, in some exemplary configurations, the elastic strands 308 may be intermittently bonded to the single continuous substrate 300 to form the layered elastic substrate 320. For example, adhesive 397 (represented by cross-hatched areas) may be applied to the elastic strands 308 intermittently in the machine direction MD. In such an example, the layered elastic substrate 320 has bonded regions 393 where the elastic strands 308 are bonded to the single continuous substrate 300 and nonbonded regions 399 where the elastic strands 308 are not bonded to the single continuous substrate 300. For the purposes of clarity, dashed lines 391 are shown in FIG. 12 to represent example boundaries between the nonbonded regions 399 and the bonded regions 393 of the layered elastic substrate 320. As shown in FIG. 13, in other exemplary configurations, the continuous elastic strands 308 may be continuously bonded to the single continuous substrate 300 to form the layered elastic substrate 320. For example, adhesive 397 (represented by cross-hatched areas) may be applied continuously to the elastic strands 308 such that when it is joined with the single continuous substrate 300, it bonds to the single continuous substrate 300 continuously along the entire length of the single continuous substrate 300. In an exemplary configuration where the first substrate layer is formed from a first continuous substrate and the second substrate layer is formed from a second continuous substrate, it is to be appreciated that the elastic material may also be intermittently or continuously bonded to the first and second continuous substrates.

Referring to FIG. 11, once the continuous length of layered elastic substrate 320 is consolidated, adhesive 397 may be applied by an adhesive applicator 387. Next, the continuous length of layered elastic substrate 320 may be cut by the cutter 298 into discrete lengths of layered elastic substrate 194 in the form of waistbands 114. The waistbands 114 may be bonded to a continuous length of absorbent articles 201 in a stretched state using a tamper apparatus 296. The continuous length of absorbent articles 201 may be cut into discrete absorbent articles 150 as shown in FIG. 3B.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making a layered elastic substrate, the method comprising the steps of:
   advancing a first elastic material in a machine direction to a first metering device at a speed, V1, wherein the first elastic material is in a stretched state;
   advancing a second elastic material in the machine direction to a second metering device at a speed, V2, wherein the second elastic material is in a stretched state;
   advancing a first substrate layer in the machine direction, the first substrate layer having a first surface and an opposing second surface;
   advancing a second substrate layer in the machine direction, the second substrate layer having a first surface and an opposing second surface;
   advancing the first elastic material, the second elastic material, the first substrate layer and the second substrate layer in the machine direction to a third metering device at a speed, V3;
   bonding the first and second elastic materials in the stretched states to the first surface of the first substrate layer and the first surface of the second substrate layer at the third metering device to form a layered elastic substrate; and
   advancing the layered elastic substrate onto a fourth metering device, wherein the fourth metering device comprises a drum rotating about an axis of rotation, the drum having an outer circumferential surface moving at speed, V4;
   cutting the layered elastic substrate disposed on the fourth metering device in a cross direction to form discrete lengths of layered elastic substrate, the discrete lengths of layered elastic substrate having a first edge region and a second edge region separated by an inner region,
   wherein V1 is less than V2, wherein V3 is greater than V1 and V2, wherein V4 is less than V3, and wherein V4 is greater than V1 and V2.

2. The method of claim 1 further comprising the step of:
   cutting the discrete length of layered elastic substrate in the machine direction along the inner region to separate the discrete length of layered elastic substrate into a first discrete length of layered elastic substrate and a second discrete length of layered elastic substrate, wherein the first discrete length of layered elastic substrate comprises the first elastic material, wherein the second discrete length of layered elastic substrate comprises the second elastic material.

3. The method of claim 2, further comprising the steps of:
   advancing a continuous length of web material in a second machine direction;
   bonding each discrete length of layered elastic substrate to the continuous length of web material, wherein the discrete lengths of layered elastic substrate are spaced apart from each other in the second machine direction; and cutting the continuous length of web material in the machine direction along the inner region of each discrete length of layered elastic substrate to separate the continuous length of web material into a first absorbent article and a second absorbent article, wherein the first absorbent article comprises the first discrete length of layered elastic substrate including the first elastic material, and wherein the second absorbent article includes the second discrete length of layered elastic substrate including the second elastic material.

4. The method of claim 3, wherein the discrete lengths of layered elastic substrate define a centerline extending in the cross direction along the inner region, and wherein the step of cutting the continuous length of web material further comprises cutting the continuous length of web material along the centerline of the discrete lengths of layered elastic substrate.

5. The method of claim 1 further comprising the steps of:
stretching the first elastic material to a first elongation between the first and the third metering devices;
stretching the second elastic material to a second elongation between the second and the third metering devices, wherein the first elongation is greater than the second elongation; and
consolidating the layered elastic substrate between the third and the fourth metering devices, wherein the first elastic material is consolidated from the first elongation to a third elongation, wherein the second elastic material is consolidated from the second elongation to a fourth elongation, wherein the fourth elongation is less than the second elongation and the third elongation is less than the first elongation.

6. The method of claim 5, wherein:
the first elongation is about 150%;
the second elongation is about 100%;
the third elongation is about 80%; and
the fourth elongation is about 20%.

7. The method of claim 1, wherein the first elastic material and the second elastic material are the same.

8. The method of claim 1, wherein:
the first elastic material comprises a first number of elastic strands; and
the second elastic material comprises a second number of elastic strands, wherein the first number of elastic strands is greater than the second number of elastic strands.

9. The method of claim 1, wherein the first elastic material has a first mass density and the second elastic material has a second mass density, wherein the first mass density is greater than the second mass density.

10. The method of claim 1, wherein:
the first metering device comprises a roller rotating about an axis of rotation, the roller having an outer circumferential surface moving at speed, V1;
the second metering device comprises a roller rotating about an axis of rotation, the roller having an outer circumferential surface moving at speed, V2; and
the third metering device comprises a first roller rotating about a first axis of rotation, the first roller having an outer circumferential surface moving at speed, V3.

11. The method of claim 10, wherein the third metering device further comprises a second roller rotating about a second axis of rotation, the second roller having an outer circumferential surface moving at speed, V3, wherein the first roller and the second roller of the third metering device rotate in opposite directions, wherein the second roller is located adjacent to the first roller to define a first nip between the first roller and the second roller.

12. The method of claim 1 further comprising the steps of:
advancing a single continuous substrate in the machine direction, the single continuous substrate having a first surface and an opposing second surface, wherein the single continuous substrate defines cross-directionally opposed first and second lateral edges and first and second edge regions separated along a cross direction by an inner region; and
forming the first and second substrate layers by folding the first surface of the first edge region of the single continuous substrate onto a portion of either the first edge region, the inner region, or the second edge region of the first surface of the single continuous substrate.

13. The method of claim 1, wherein the step of bonding the first and second elastic materials in the stretched states to the first surface of the first substrate layer and the first surface of the second substrate layer further comprises intermittently bonding the first and second elastic materials to form a layered elastic substrate having bonded regions and nonbonded regions,
wherein the layered elastic substrate is cut along the nonbonded regions into discrete lengths of layered elastic substrate, wherein the first and second elastic materials cut along the nonbonded regions retract to the bonded regions.

14. The method of claim 3, wherein:
the first discrete length of layered elastic substrate is a first waistband;
the second discrete length of layered elastic substrate is a second waistband; and
the continuous length of web material is a continuous length of absorbent articles.

15. A method for making layered elastic substrates, the method comprising the steps of:
advancing a first elastic material in a machine direction to a first metering device at a speed, V1, wherein the first elastic material is in a stretched state;
advancing a second elastic material in the machine direction to a second metering device at a speed, V2, wherein the second elastic material is in a stretched state;
advancing a continuous substrate in the machine direction, the substrate having a first surface and an opposing second surface, the substrate defining a first edge region and a second edge region separated by a inner region along a cross direction;
folding the substrate to position the first surface of the first edge region into a facing relationship with the first surface of the inner region;
folding the substrate to position the first surface of the second edge region into a facing relationship with the first surface of the inner region;
advancing the first elastic material, the second elastic material, and the continuous substrate in the machine direction to a third metering device at a speed, V3;
bonding the first and second elastic materials in the stretched states to the continuous substrate at the third metering device to form a layered elastic substrate; and
advancing the layered elastic substrate onto a fourth metering device, wherein the fourth metering device comprises a drum rotating about an axis of rotation, the drum having an outer circumferential surface moving at a speed, V4;
cutting the layered elastic substrate disposed on the fourth metering device in a cross direction to form discrete lengths of layered elastic substrate, the discrete lengths of layered elastic substrate having a first edge region and a second edge region separated by an inner region,
wherein V1 is less than V2, wherein V3 is greater than V1 and V2, wherein V4 is less than V3, and wherein V4 is greater than V1 and V2.

16. The method of claim 15 further comprising the steps of:
advancing a continuous length of web material in a second machine direction;
bonding the discrete lengths of layered elastic substrate to the continuous length of web material, wherein the discrete lengths of layered elastic substrate are spaced apart in the second machine direction; and
cutting the continuous length of web material in the machine direction along the inner region of the discrete lengths of layered elastic substrate to separate the continuous length of web material into a first absorbent article and a second absorbent article, wherein the first absorbent article comprises a first discrete length of layered elastic substrate including the first elastic material, and wherein the second absorbent article comprises a second discrete length of layered elastic substrate including the second elastic material.

17. The method of claim 15 wherein the step of folding the substrate to position the first surface of the second edge region of the continuous substrate into facing relationship with the first surface of the inner region of the continuous substrate further comprises folding the substrate to position the first surface of the second edge region of the continuous substrate into a facing relationship with the second surface of the first edge region of the continuous substrate.

18. The method of claim 15 further comprising the steps of:
stretching the first elastic material to a first elongation between the first and the third metering devices;
stretching the second elastic material to a second elongation between the second and the third metering devices, wherein the first elongation is greater than the second elongation; and
consolidating the layered elastic substrate between the third and the fourth metering devices, wherein the first elastic material is consolidated from the first elongation to a third elongation, wherein the third elongation is less than the first elongation, wherein the second elastic material is consolidated from the second elongation to a fourth elongation, and wherein the fourth elongation is less than the second elongation.

19. The method of claim 15, wherein the first elastic material has a first mass density and the second elastic material has a second mass density, wherein the first mass density is greater than the second mass density.

20. The method of claim 15, wherein the first elastic material comprises a first number of elastic strands and the second elastic material comprises a second number of elastic strands, wherein the first number of elastic strands is greater than the second number of elastic strands.

* * * * *

UNITED STATES PATENT AND TRADEMARK OFFICE
CERTIFICATE OF CORRECTION

| | | |
|---|---|---|
| PATENT NO. | : 9,226,858 B2 | Page 1 of 1 |
| APPLICATION NO. | : 13/929878 | |
| DATED | : January 5, 2016 | |
| INVENTOR(S) | : Raymond Scott Hamilton et al. | |

It is certified that error appears in the above-identified patent and that said Letters Patent is hereby corrected as shown below:

Title page

Item (74) Attorney, Agent or Firm should read: Abbey A. Lopez

Signed and Sealed this
Nineteenth Day of April, 2016

Michelle K. Lee
*Director of the United States Patent and Trademark Office*